United States Patent
Hama et al.

(10) Patent No.: US 9,814,656 B2
(45) Date of Patent: Nov. 14, 2017

(54) POROUS RESIN PARTICLES, METHOD OF MANUFACTURING POROUS RESIN PARTICLES, AND USE OF POROUS RESIN PARTICLES

(71) Applicant: Sekisui Plastics Co., Ltd., Osaka-shi (JP)

(72) Inventors: Yukio Hama, Koka (JP); Koichiro Okamoto, Koka (JP); Junko Hiroi, Koka (JP)

(73) Assignee: Sekisui Plastics Co., Ltd., Osaka-shi (JP)

(*) Notice: Subject to any disclaimer, the term of this patent is extended or adjusted under 35 U.S.C. 154(b) by 0 days.

(21) Appl. No.: 14/382,631

(22) PCT Filed: Mar. 29, 2013

(86) PCT No.: PCT/JP2013/059749
§ 371 (c)(1),
(2) Date: Sep. 3, 2014

(87) PCT Pub. No.: WO2014/050177
PCT Pub. Date: Apr. 3, 2014

(65) Prior Publication Data
US 2015/0030842 A1    Jan. 29, 2015

(30) Foreign Application Priority Data
Sep. 26, 2012  (JP) ................ 2012-212419

(51) Int. Cl.
*C08J 9/28* (2006.01)
*A61K 8/02* (2006.01)
(Continued)

(52) U.S. Cl.
CPC .......... *A61K 8/0279* (2013.01); *A61K 8/8152* (2013.01); *A61Q 1/02* (2013.01);
(Continued)

(58) Field of Classification Search
CPC ..... C08J 9/286; C08J 2333/10; A61K 8/0279; A61K 8/37; A61K 2800/41
(Continued)

(56) References Cited

U.S. PATENT DOCUMENTS 6,254,990 B1 *   7/2001   Ishizaki et al. ............... 428/402
6,362,245 B1 *   3/2002   Takahashi et al. ........... 521/149
(Continued)

FOREIGN PATENT DOCUMENTS

JP     50-12176 A    2/1975
JP     57-098205 A   6/1982
(Continued)

OTHER PUBLICATIONS

Ute et al., Glass transition temperature and melting temperature of uniform isotactic and syndiotactic poly(methyl methacrylate)s from 13mer to 50mer (Polymer vol. 36, No. 7, pp. 1415-1419, 1995).*
(Continued)

*Primary Examiner* — Holly Le
(74) *Attorney, Agent, or Firm* — Locke Lord LLP; James E. Armstrong, IV; Nicholas J. DiCeglie, Jr.

(57) ABSTRACT

Disclosed are porous resin particles which contain a polymer of a monomer mixture containing, as monomers, at least a monofunctional (meth)acrylic acid ester and a crosslinking monomer. The monofunctional (meth)acrylic acid ester accounts for 1 wt % to 50 wt % of the monomer mixture, and the crosslinking monomer accounts for 50 wt % to 99 wt % of the monomer mixture. The porous resin particles have a specific surface area of 190 $m^2/g$ to 300 $m^2/g$ and a bulk specific gravity of 0.25 g/mL to 0.45 g/mL.

22 Claims, 1 Drawing Sheet

(51) Int. Cl.
A61Q 1/02 (2006.01)
A61Q 1/12 (2006.01)
C08J 3/12 (2006.01)
A61K 8/81 (2006.01)
B01J 20/28 (2006.01)
B01J 20/30 (2006.01)
C08J 9/26 (2006.01)
G02B 1/111 (2015.01)
C08F 222/10 (2006.01)
C09D 133/10 (2006.01)

(52) U.S. Cl.
CPC .......... *A61Q 1/12* (2013.01); *B01J 20/28061* (2013.01); *B01J 20/3064* (2013.01); *C08F 222/1006* (2013.01); *C08J 3/12* (2013.01); *C08J 9/26* (2013.01); *C08J 9/28* (2013.01); *C08J 9/286* (2013.01); *G02B 1/111* (2013.01); *A61K 2800/654* (2013.01); *C08J 2333/10* (2013.01); *C08J 2333/12* (2013.01); *C08J 2333/14* (2013.01); *C08L 2312/00* (2013.01); *C09D 133/10* (2013.01); *Y10T 428/249953* (2015.04)

(58) Field of Classification Search
USPC .................................. 428/402, 482; 521/65
See application file for complete search history.

(56) References Cited

U.S. PATENT DOCUMENTS

| 8,696,099 B2 | 4/2014 | Ozawa | |
|---|---|---|---|
| 2010/0311850 A1* | 12/2010 | Wickert et al. | 521/61 |
| 2012/0034281 A1 | 2/2012 | Kaneko et al. | |

FOREIGN PATENT DOCUMENTS

| JP | 08-059436 A | 3/1996 |
|---|---|---|
| JP | 2909078 B2 | 6/1999 |
| JP | 2002-265529 A | 9/2002 |
| JP | 2003-081738 A | 3/2003 |
| JP | 2004-099700 A | 4/2004 |
| JP | 2005-154585 A | 6/2005 |
| JP | 2012-071485 A | 4/2012 |
| WO | WO-2010/114125 A1 | 10/2010 |

OTHER PUBLICATIONS

International Search Report dated May 7, 2013, issued for PCT/JP2013/059749.

* cited by examiner

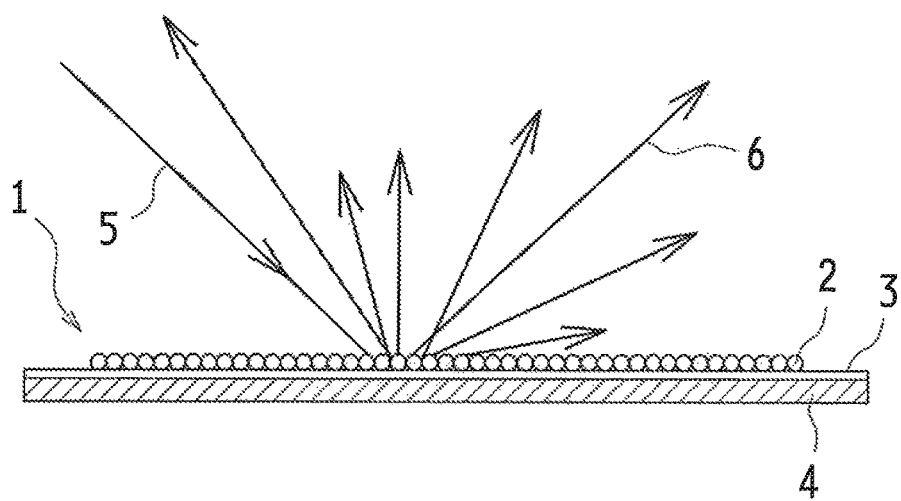

POROUS RESIN PARTICLES, METHOD OF MANUFACTURING POROUS RESIN PARTICLES, AND USE OF POROUS RESIN PARTICLES

TECHNICAL FIELD

The present invention relates to porous resin particles, a method of manufacturing the porous resin particles, and use of the porous resin particles (e.g., external preparations, coating agents, optical films, resin compositions, and molded objects).

BACKGROUND ART

Spherical particles have been conventionally compounded to form, among others, makeup preparations (e.g., makeup foundations, makeup powders, cheek colors, and eye shadows), external preparations for body (e.g., body powders and baby powders), and lotion preparations (e.g., pre-shave lotions and body lotions) to improve their spreadability and feel on the skin and impart to them a soft-focus property that makes, for example, skin pores, colored skin spots, and wrinkles less visually recognizable.

As an example, Patent Document 1 discloses a cosmetic preparation obtained by compounding silica powder, a carboxyvinyl polymer, and an oil material. The silica powder contained in the cosmetic preparation disclosed in Patent Document 1 is spherical and readily irregularly reflects (diffuses) light. Compounding this silica powder into the cosmetic preparation imparts a soft-focus property to the cosmetic preparation. The silica powder, also possessing an oil absorbing property, absorbs sebum secreted from the skin to restrain the cosmetic preparation from smearing due to sebum being mixed with, for example, oils and active agents in the cosmetic preparation.

Patent Document 2 discloses a cosmetic preparation obtained by compounding spherical porous powder having a particle diameter of 1 μm to 40 μm and an average particle diameter of 2 μm to 20 μm. The spherical porous powder compounded into a cosmetic preparation disclosed in Patent Document 2, likewise possessing an oil absorbing property, restrains the cosmetic preparation, especially, a makeup preparation, from smearing.

Patent Document 3 discloses a particulate solid cosmetic preparation containing spherical poly(meth)acrylate particles that have hollow pores both inside and on their surfaces. The spherical poly(meth)acrylate particles have an average particle diameter of 3 μm to 20 μm, a specific surface area of 80 m$^2$/g to 180 m$^2$/g, and a most frequent pore diameter of 180 Å or larger. The spherical poly(meth) acrylate particles disclosed in Patent Document 2, likewise possessing an oil absorbing property, restrain a cosmetic preparation from smearing similarly to the spherical porous powder disclosed in Patent Document 3. In addition, the spherical poly(meth)acrylate particles readily irregularly reflect light. Compounding the spherical poly(meth)acrylate particles into the cosmetic preparation imparts a soft-focus property to the cosmetic preparation.

CITATION LIST

Patent Literature

Patent Document 1: Japanese Patent Application Publication, Tokukaihei, No. 8-59436

Patent Document 2: Japanese Patent Application Publication, Tokukaisho, No. 57-98205

Patent Document 3: PCT International Application Publication, No. WO2010/114125

SUMMARY OF THE INVENTION

Problems to be Solved by the Invention

The silica powder contained in the cosmetic preparation disclosed in Patent Document 1, however, does not have a sufficient oil absorbing property to restrain makeup smearing over an extended period of time. Specifically, the silica powder indeed absorbs sebum, but only in as little as 20 mL/100 g to 50 mL/100 g, and is incapable of continuously absorbing sebum over an extended period of time. Therefore, compounding the silica powder into the cosmetic preparation would not effectively restrain makeup smearing over an extended period of time or improve makeup lasting time.

The spherical porous powder contained in the cosmetic preparation disclosed in Patent Document 2 has a better oil absorbing property than the silica powder. The oil absorption amount for the spherical porous powder (74.6 mL/100 g to 78.3 mL/100 g) is still not sufficient to restrain makeup smearing over an extended period of time. In addition, the spherical porous powder disclosed in Patent Document 2 scatters (diffuses) little light on its surface, falling short of imparting an excellent soft-focus property to cosmetic preparations.

The spherical poly(meth)acrylate particles contained in the cosmetic preparation disclosed in in Patent Document 3 impart an excellent soft-focus property to cosmetic preparations. The spherical poly(meth)acrylate particles, with a superior oil absorbing property to the silica powder and the spherical porous powder, continuously absorbs sebum over an extended period of time. The cosmetic preparations disclosed in Patent Document 3 therefore lasts longer than the cosmetic preparations disclosed in Patent Documents 1 and 2. Recent years have seen demand, however, for cosmetic preparations that last even longer. That in turn creates demand for an improved oil absorbing property in spherical particles that are compounded to impart a soft-focus property to cosmetic preparations.

Such spherical particles are expected to be used broadly not only as ingredients for cosmetic and other external preparations, but also as additives that impart light diffusion properties to coating agents (e.g., coating materials), optical films (e.g., anti-glare films and light diffusion films), and light diffusion members (e.g., lighting covers, light diffusion sheets, and light diffusion plates).

The present invention, conceived in view of these problems, has an object to provide porous resin particles with excellent light diffusion and oil absorbing properties, a method of manufacturing the porous resin particles, and use of the porous resin particles.

Solution to Problem

The present invention is directed to porous resin particles which contain a polymer of a monomer mixture containing, as monomers, at least a monofunctional (meth)acrylic acid ester and a crosslinking monomer, the monofunctional (meth)acrylic acid ester accounting for 1 wt % to 50 wt % of the monomer mixture, the crosslinking monomer accounting for 50 wt % to 99 wt % of the monomer mixture, and the porous resin particles having a specific surface area of 190 m²/g to 300 m²/g and a bulk specific gravity of 0.25 g/mL to 0.45 g/mL.

The porous resin particles of the present invention have numerous pores with a specific surface area as high as 190 m²/g to 300 m²/g, thereby exhibiting both excellent light diffusion and oil absorbing properties. The porous resin particles of the present invention, with their excellent light diffusion properties, impart to cosmetic and other external preparations a soft-focus property that makes, for example, skin pores, wrinkles, and colored skin spots less visually recognizable when compounded into those external preparations. The porous resin particles of the present invention also have an oil absorbing property, and when compounded into an external preparation, absorb sebum secreted from the skin to which the external preparation is applied, thereby making smooth skin. The porous resin particles also exhibit a high oil absorption amount and continuously absorb sebum over an extended period of time. Hence, the porous resin particles, when compounded into a cosmetic preparation, reduce glaring and improve makeup lasting time. In addition, the porous resin particles have a bulk specific gravity as low as 0.25 g/mL to 0.45 g/mL, and when compounded into a cosmetic or like external preparation, improve spread (i.e., spreadability) of the external preparation on the skin. The porous resin particles of the present invention also have excellent light diffusion properties as mentioned above, and when compounded into a coating agent, optical film, or light diffusion member, impart such light diffusion properties to the coating agent, optical film, or light diffusion member. Note that the term, "light diffusion properties," as used in the present specification refers to both the diffusibility of reflected light and of transmitted light.

The present invention is directed also to porous resin particles which have a specific surface area of 190 m²/g to 300 m²/g and such optical properties that the porous resin particles reflect, in a 0° direction with an intensity of 45 or greater, light that is incident thereto at an angle of −45°, where the porous resin particles specularly reflect, in a +45° direction with an intensity of 100, light that is incident thereto at an angle of −45°.

These porous resin particles of the present invention also have numerous pores with a specific surface area as high as 190 m²/g to 300 m²/g, thereby exhibiting both excellent light diffusion and oil absorbing properties. In other words, the porous resin particles of the present invention, with their excellent light diffusion properties, impart to cosmetic and other external preparations a soft-focus property that makes, for example, skin pores, wrinkles, and colored skin spots less visually recognizable when compounded into those external preparations. The porous resin particles of the present invention also have an oil absorbing property, and when compounded into an external preparation, absorb sebum secreted from the skin to which the external preparation is applied, thereby making smooth skin. The porous resin particles also exhibit a high oil absorption amount and continuously absorb sebum over an extended period of time. Hence, the porous resin particles, when compounded into a cosmetic preparation, reduce glaring and improve makeup lasting time. In addition, the porous resin particles of the present invention have excellent light diffusion properties as mentioned above, and when compounded into a coating agent, optical film, or light diffusion member, impart such light diffusion properties to the coating agent, optical film, or light diffusion member.

The present invention is directed also to a method of manufacturing porous resin particles which includes: the polymerization step of suspension polymerizing a monomer mixture containing 1 wt % to 50 wt % monofunctional (meth)acrylic acid ester and 50 wt % to 99 wt % crosslinking monomer in an aqueous medium in the presence of an organic solvent to prepare a suspension containing porous resin particles; and the distillation step of distilling the suspension to remove the organic solvent from the suspension after the polymerization step, the organic solvent being used in 180, exclusive, to 450 parts by weight per 100 parts by weight of the monomer mixture in the polymerization step.

According to this method of manufacturing porous resin particles of the present invention, a monomer mixture containing 1 wt % to 50 wt % monofunctional (meth)acrylic acid ester and 50 wt % to 99 wt % crosslinking monomer is polymerized in the presence of 180, exclusive, to 450 parts by weight of an organic solvent per 100 parts by weight of the monomer mixture. Therefore, the manufactured porous resin particles have numerous pores with excellent light diffusion and oil absorbing properties and a low bulk specific gravity. In other words, the porous resin particles manufactured by the method of manufacturing of the present invention have excellent light diffusion properties and hence impart to cosmetic and other external preparations a soft-focus property that makes, for example, skin pores, wrinkles, and colored skin spots less visually recognizable when compounded into those external preparations. The porous resin particles manufactured by the method of manufacturing of the present invention also have an oil absorbing property, and when compounded into an external preparation, absorb sebum secreted from the skin to which the external preparation is applied, thereby making smooth skin. The porous resin particles also exhibit a high oil absorption amount and continuously absorb sebum over an extended period of time. Hence, the porous resin particles, when compounded into a cosmetic preparation, reduce glaring and improve makeup lasting time. In addition, the porous resin particles manufactured by the method of manufacturing of the present invention have numerous pores and a low bulk specific gravity, and when compounded into a cosmetic or like external preparation, improve spread (i.e., spreadability) of the external preparation on the skin. In addition, the porous resin particles manufactured by the method of manufacturing of the present invention have excellent light diffusion properties as mentioned above, and when compounded into a coating agent, optical film, or light diffusion member, impart such light diffusion properties to the coating agent, optical film, or light diffusion member.

The present invention is directed also to an external preparation which contains the aforementioned porous resin particles of the present invention.

This external preparation of the present invention, containing the porous resin particles of the present invention, has an excellent soft-focus property that makes, for example, skin pores, wrinkles, and colored skin spots less visually recognizable by multiple scattering (diffusion) of light. The external preparation is excellent also in making smooth skin by absorbing sebum and in spreadability. In addition, the external preparation of the present invention, being capable of continuously absorbing sebum over an extended period of time, exhibits an excellent makeup lasting time when the external preparation of the present invention is a cosmetic preparation.

The present invention is directed also to a coating agent which contains the aforementioned porous resin particles of the present invention.

This coating agent of the present invention, containing the porous resin particles of the present invention that have excellent light diffusion properties, has excellent light diffusion properties, and when used as a finish coating material, exhibits excellent matting properties.

The present invention is directed also to an optical film which contains a base material and the aforementioned coating agent, the base material being coated with the coating agent.

The optical film of the present invention, being coated with the coating agent of the present invention that has excellent light diffusion properties, has excellent light diffusion properties.

The present invention is directed also to a resin composition which contains a base resin and the aforementioned porous resin particles of the present invention.

The resin composition of the present invention, containing the porous resin particles of the present invention that have excellent light diffusion properties, has excellent light diffusion properties.

The present invention is directed also to a molded object which contains the aforementioned resin composition of the present invention, the resin composition being molded into the molded object.

The molded object of the present invention, being molded from the resin composition of the present invention that has excellent light diffusion properties, has excellent light diffusion properties.

Advantageous Effects of the Invention

The present invention provides porous resin particles with excellent light diffusion and oil absorbing properties, a method of manufacturing the porous resin particles, and use of the porous resin particles (external preparations, coating agents, optical films, resin compositions, and molded objects).

BRIEF DESCRIPTION OF DRAWINGS

FIG. 1 is a conceptual drawing of a ray of incident light and its reflections off a test piece for evaluation of its light diffusion properties.

DESCRIPTION OF EMBODIMENTS

Porous Resin Particles

Porous resin particles of the present invention have numerous pores with a specific surface area of 190 $m^2/g$ to 300 $m^2/g$. These porous resin particles of the present invention exhibit both excellent light diffusion and oil absorbing properties.

As an example, the porous resin particles of the present invention contain a polymer of a monomer mixture containing, as monomers, at least a monofunctional (meth)acrylic acid ester and a crosslinking monomer. The monofunctional (meth)acrylic acid ester accounts for 1 wt % to 50 wt % of the monomer mixture. The crosslinking monomer accounts for 50 wt % to 99 wt % of the monomer mixture. The porous resin particles of the present invention have a specific surface area of 190 $m^2/g$ to 300 $m^2/g$ and a bulk specific gravity of 0.25 g/mL to 0.45 g/mL. Throughout the present specification, "(meth)acrylic" refers to either methacrylic or acrylic.

Other porous resin particles of the present invention have a specific surface area of 190 $m^2/g$ to 300 $m^2/g$ and such optical properties that the porous resin particles reflect, in a 0° direction with an intensity of 45 or greater, light that is incident thereto at an angle of −45°, where the porous resin particles specularly reflect, in a +45° direction with an intensity of 100, light that is incident thereto at an angle of −45°.

The quantification and qualitative analysis of structural units derived from each monomer in the porous resin particles of the present invention may be checked by a publicly known analysis method, such as gas chromatography, liquid chromatography, infrared spectroscopy (IR spectroscopy), or nuclear magnetic resonance spectroscopy (NMR spectroscopy). The weight ratio of each monomer in the monomer mixture is substantially equal to the weight ratio of a structural unit derived from that monomer in the porous resin particles of the present invention.

The aforementioned monofunctional (meth)acrylic acid ester may be any publicly known (meth)acrylic acid ester with a single unsaturated ethylenic group, or with an unsaturated ethylenic group only in the (meth)acrylic group, provided that it does not affect the specific surface area of the porous resin particles of the present invention.

Examples of the monofunctional (meth)acrylic acid ester include methyl (meth)acrylate, ethyl (meth)acrylate, propyl (meth)acrylate, butyl (meth)acrylate, pentyl (meth)acrylate, hexyl (meth)acrylate, heptyl (meth)acrylate, octyl (meth) acrylate, nonyl (meth)acrylate, decyl (meth)acrylate, undecyl (meth)acrylate, dodecyl (meth)acrylate, glycidyl (meth) acrylate, methoxyethyl (meth)acrylate, propoxyethyl (meth) acrylate, butoxyethyl (meth)acrylate, methoxy diethylene glycol (meth)acrylate, ethoxy diethylene glycol (meth)acrylate, methoxy ethylene glycol (meth)acrylate, butoxy triethylene glycol (meth)acrylate, methoxy dipropylene glycol (meth)acrylate, phenoxyethyl (meth)acrylate, phenoxy diethylene glycol (meth)acrylate, phenoxy tetraethylene glycol (meth)acrylate, benzyl (meth)acrylate, cyclohexyl (meth)acrylate, tetrahydrofurfuryl (meth)acrylate, dicyclopentenyl (meth)acrylate, dicyclopentenyloxyethyl (meth) acrylate, N-vinyl-2-pyrrolidone (meth)acrylate, 2-hydroxyethyl (meth)acrylate, hydroxypropyl (meth)acrylate, hydroxybutyl (meth)acrylate, and 2-hydroxy-3-phenyl oxypropyl (meth)acrylate. Any one of these monofunctional (meth)acrylic acid esters may be used alone; alternatively, two or more of them may be used in any combination. The monofunctional (meth)acrylic acid ester used in the present invention is preferably a $C_1$-$C_4$ alkyl ester of a (meth)acrylic acid, especially, methyl methacrylate.

The aforementioned crosslinking monomer may be a publicly known crosslinking monomer with two or more unsaturated ethylenic groups.

Examples of the aforementioned crosslinking monomer include (meth)acrylic-based crosslinking monomers, such as ethylene glycol di(meth)acrylate, 1,6-hexanediol di(meth) acrylate, allyl (meth)acrylate, trimethylolpropane tri(meth) acrylate, and pentaerythritol tetra(meth)acrylate; divinyl benzene; divinyl naphthalene; diallyl phthalate; and vinyl-based crosslinking monomers that are derivatives of these compounds. Among these compounds, a (meth)acrylic-based crosslinking monomer is preferred, and ethylene glycol di(meth)acrylate is more preferred. Any one of these crosslinking monomers may be used alone; alternatively, two or more of them may be used in any combination. Throughout the present specification, "(meth)acrylate" refers to either methacrylate or acrylate.

The monofunctional (meth)acrylic acid ester accounts for 1 wt % to 50 wt %, preferably 10 wt % to 50 wt %, of the monomer mixture. If the monofunctional (meth)acrylic acid ester accounts for 1 wt % to 50 wt % of the monomer mixture, the monomer mixture is capable of containing the crosslinking monomer in a sufficient amount, thereby imparting sufficient porosity, hence large specific surface area, to the porous resin particles and reducing the bulk specific gravity of the porous resin particles.

The crosslinking monomer accounts for 50 wt % to 99 wt %, preferably 50 wt % to 90 wt %, of the monomer mixture. If the crosslinking monomer accounts for 50 wt % to 99 wt % of the monomer mixture, the crosslinking monomer imparts sufficient porosity, hence large specific surface area, to the porous resin particles and reduces the bulk specific gravity of the porous resin particles.

The monomer mixture may contain any monomer other than the aforementioned monofunctional (meth)acrylic acid esters and crosslinking monomers, provided that it does not affect the specific surface area of the porous resin particles of the present invention.

The porous resin particles of the present invention have a specific surface area of 190 $m^2/g$ to 300 $m^2/g$. If the specific surface area is 190 $m^2/g$ to 300 $m^2/g$, the porous resin particles are capable of absorbing oil in large amounts and exhibiting excellent light diffusion properties. Throughout the present specification, the "specific surface area" refers to surface area per unit weight, which in the present invention may be measured by BET ($N_2$). Measurement of specific surface area by BET ($N_2$) will be described in examples of the invention.

The porous resin particles of the present invention preferably have a bulk specific gravity of 0.25 g/mL to 0.45 g/mL. If the bulk specific gravity is 0.25 g/mL to 0.45 g/mL, it is ensured that the porous resin particles have sufficient particle strength. Furthermore, the porous resin particles, when compounded into an external preparation, impart sufficient spreadability to the external preparation. Throughout the present specification, the "bulk specific gravity" refers to the packed apparent specific gravity, which may be measured using a PT-E powder tester manufactured by Hosokawa Micron Corporation. Measurement of bulk specific gravity will be described in examples of the invention.

The porous resin particles of the present invention preferably have an oil absorption amount of 200 mL/100 g to 700 mL/100 g. If the oil absorption amount is 200 mL/100 g to 700 mL/100 g, the porous resin particles, when compounded into an external preparation, unfailingly impart to the external preparation a property that it can continuously absorb sebum over an extended period of time. Measurement of oil absorption amount will be described in examples of the invention.

The porous resin particles of the present invention preferably have a pore volume of 0.4 mL/g to 0.9 mL/g. If the pore volume is 0.4 mL/g to 0.9 mL/g, the porous resin particles unfailingly have sufficient oil absorbing and light diffusion properties. Throughout the present specification, the "pore volume" refers to pore volume per unit weight, which in the present invention may be measured from the nitrogen desorption isotherm by BJH. Measurement of pore volume will be described in examples of the invention.

The porous resin particles of the present invention have an average pore diameter of preferably 10 nm to 18 nm, more preferably 12 nm to 16 nm, even more preferably 13 nm to 16 nm, and still more preferably 14 nm to 15 nm. If the average pore diameter is less than 10 nm, the porous resin particles may be too solid to retain their particulate properties (e.g., high water and oil adsorption, low bulk specific gravity, and multiple scattering (diffusion) of light). If the average pore diameter is greater than 18 nm, the porous resin particles may have too much hollow internal space to retain its sufficient particle strength. The "average pore diameter" refers to the average pore diameter as measured from the nitrogen desorption isotherm by BJH. Measurement of average pore diameter will be described in examples of the invention.

The porous resin particles of the present invention, when compressed by 10%, have a compression strength of preferably 3.0 MPa to 7.0 MPa and more preferably 3.5 MPa to 6.0 MPa. If the porous resin particles have a compression strength of less than 3.0 MPa when compressed by 10%, the porous resin particles may be so solid that they could impart a hard texture when compounded into a cosmetic preparation. If the porous resin particles have a compression strength in excess of 7.0 MPa when compressed by 10%, the porous resin particles, when compounded into an external preparation, could impart insufficient spreadability, hence a hard feel, to the external preparation. Throughout the present specification, the "compression strength" refers to the compression strength of the porous resin particles being compressed by 10%, or more specifically, the strength of the porous resin particles being placed under such a load that their particle diameter changes by 10% (S10 strength). Measurement of compression strength (S10 strength) will be described in examples of the invention.

Letting the intensity of 100 represent that of a specular +45°-direction reflection, off the porous resin particles of the present invention, of light that is incident to the porous resin particles at an angle of −45°, the porous resin particles have such optical properties that the porous resin particles reflect, in a 0° direction with an intensity of 45 or greater, preferably 55 or greater, light that is incident thereto at an angle of −45°. If the porous resin particles reflect, in a 0° direction with an intensity of less than 45, light that is incident thereto at an angle of −45°, the porous resin particles may not cause sufficient multiple scattering (diffusion) of incident light, and when compounded into an external preparation, could fail to impart a sufficient soft-focus property to the external preparation. An evaluation method for light diffusion properties based on the intensity of reflected light will be described in examples of the invention.

The porous resin particles of the present invention have a volume-average particle diameter of preferably 1 μm to 100 μm and more preferably 4 μm to 20 μm. If the volume-average particle diameter is within these ranges, the porous resin particles of the present invention effectively exhibit distinct properties of porous resin particles (e.g., multiple light scattering (light diffusion properties)).

The porous resin particles of the present invention preferably do not contain much unreacted, residual monofunctional (meth)acrylic acid ester (e.g., less than 30 ppm). If the porous resin particles do not contain much unreacted, residual monofunctional (meth)acrylic acid ester, molding defects, such as yellowing and gum, are reduced when a resin composition prepared by kneading the resin particles into a base resin is molded by, for example, extrusion molding or injection molding into a molded object. Throughout the present specification, "gum" refers to burnt resin that accumulates around a die over time in extrusion of a plastic (resin composition).

Since the porous resin particles of the present invention have pores, they are suited for use as, for example, an additive (e.g., flatting agent, coating film softening agent, designing agent) for coating agents (coating compositions) used as general coating materials or coating agents for paper, information recording paper, or optical members (e.g., optical films); a light diffusion agent mixed into resin compositions for manufacturing molded objects, such as light diffusers (e.g., lighting covers, light diffusion plates, light diffusion films); a blocking preventing agent for films, such as food wrapping films; an additive to cosmetics and other external preparations (additive for improved spreadability, sebum absorption, or clearance of colored skin spots, wrinkles, and other like skin problems).

Method of Manufacturing Porous Resin Particles

The porous resin particles of the present invention are manufactured by a method of manufacturing porous resin particles which involves: the polymerization step of suspension polymerizing a monomer mixture containing 1 wt % to 50 wt % monofunctional (meth)acrylic acid ester and 50 wt % to 99 wt % crosslinking monomer in an aqueous medium in the presence of an organic solvent to prepare a suspension containing porous resin particles; and the distillation step of distilling the suspension to remove the organic solvent from the suspension after the polymerization step, the organic solvent being used in 180, exclusive, to 450 parts by weight per 100 parts by weight of the monomer mixture in the polymerization step.

The following will describe the polymerization step and the distillation step in detail.

Polymerization Step

In the polymerization step, a monomer mixture containing 1 wt % to 50 wt % monofunctional (meth)acrylic acid ester and 50 wt % to 99 wt % crosslinking monomer is suspension polymerized in an aqueous medium in the presence of an organic solvent to prepare a suspension containing porous resin particles. The suspension polymerization in this polymerization step may be carried out by, for example, dispersing droplets of a mixture (oil phase) containing the monomer mixture and the organic solvent in an aqueous phase containing the aqueous medium and polymerizing the monomer mixture.

The aqueous medium is by no means limited in any particular manner. Examples include water and mixed media of water and a water-soluble organic medium (methanol, ethanol, or other lower alcohols (alcohols with 5 or fewer carbon atoms)). The aqueous medium is typically used in an amount of 100 to 1,000 parts by weight per 100 parts by weight of the monomer mixture to stabilize the porous resin particles.

As mentioned above, the monomer mixture contains, as monomers, at least the monofunctional (meth)acrylic acid ester and the crosslinking monomer. As mentioned above, the monofunctional (meth)acrylic acid ester accounts for 1 wt % to 50 wt % of the monomer mixture, and the crosslinking monomer accounts for 50 wt % to 99 wt % of the monomer mixture. The monomer mixture may contain, as mentioned above, any monomer other than the monofunctional (meth)acrylic acid ester and the crosslinking monomer.

The organic solvent is by no means limited in any particular manner as long as it acts as a pore forming agent. Preferably, the organic solvent is highly miscible with the monomer mixture and poorly soluble in water. Examples of such organic solvents include aromatic compounds, such as toluene and benzene; ester-based compounds, such as ethyl acetate and butyl acetate; and saturated aliphatic hydrocarbons, such as n-heptane, n-hexane, and n-octane. Some of these exemplary compounds have a boiling point of 70° C. to 90° C.: for example, benzene (boiling point: 80° C.), n-hexane (69° C.), and ethyl acetate (77° C.). Use of an organic solvent with a boiling point of 700° C. to 90° C. enables stable suspension in the polymerization step and easy removal of the organic solvent by distillation in the distillation step. Any one of the organic solvents listed here as examples may be used alone; alternatively, two or more of them may be used in any combination.

The organic solvent is used in 180, exclusive, to 450 parts by weight, preferably 200 parts by weight to 400 parts by weight, per 100 parts by weight of the monomer mixture. If the organic solvent is used in an amount outside the range of 180, exclusive, to 450 parts by weight per 100 parts by weight of the monomer mixture, the resultant porous resin particles may not have a specific surface area that is unique to the porous resin particles of the present invention.

The suspension polymerization is typically carried out in the presence of a polymerization initiator. For example, preferably, a polymerization initiator is added to the mixture (oil phase) containing the monomer mixture and the organic solvent. The polymerization initiator is by no means limited in any particular manner as long as it can initiate polymerization of the monomer mixture. Preferably used in terms of relationship with the organic solvent are substances having a 10-hour half-life period temperature of 40 to 80° C.: for example, organic peroxides, such as benzoyl peroxide, lauroyl peroxide, and t-butylperoxy 2-ethylhexanoate; and azo-based nitrile compounds, such as 2,2'-azobisisobutyronitrile, 2,2'-azobis(2-methylbutyronitrile), and 2,2'-azobis(2,4-dimethylvaleronitrile). Any one of these polymerization initiators may be used alone; alternatively, two or more of them may be used in any combination.

The polymerization initiator is used in an amount of preferably 0.01 parts by weight to 10 parts by weight, more preferably 0.01 parts by weight to 5 parts by weight, per 100 parts by weight of the monomer mixture. If the polymerization initiator is used in an amount of less than 0.01 parts by weight per 100 parts by weight of the monomer mixture, the polymerization initiator may fail to initiate sufficient polymerization. If the polymerization initiator is used in an amount of more than 10 parts by weight per 100 parts by weight of the monomer mixture, the excess use is not cost effective.

The suspension polymerization is preferably carried out in the presence of a dispersion stabilizing agent for more stable manufacture of desirable porous resin particles. For example, a dispersion stabilizing agent is added to an aqueous phase containing the aqueous medium. Examples of the dispersion stabilizing agent include inorganic oxides, such as silica and zirconium oxide; poorly water-soluble inorganic salts, such as barium carbonate, calcium carbonate, tribasic calcium phosphate, calcium pyrophosphate, calcium sulfate, magnesium hydroxide, magnesium pyrophosphate, and colloidal silica; and inorganic polymer substances, such as talc, bentonite, silicic acid, diatomaceous earth, and clay. Some of these substances are decomposed in acid and dissolved in water: for example, calcium carbonate, tribasic calcium phosphate, magnesium hydroxide, magnesium pyrophosphate, and calcium pyrophosphate. Use of these exemplary substances enables easy removal of the dispersion stabilizing agent after the polymerization step. Among these substances, magnesium pyrophosphate prepared by double decomposition is preferably used as a dispersion stabilizing agent to obtain porous resin particles with consistent particle diameters (especially, porous resin particles with a coefficient of variation of particle diameters of 40% or less).

The dispersion stabilizing agent is used in an amount of preferably 0.1 parts by weight to 20 parts by weight, more preferably 0.5 parts by weight to 10 parts by weight, per 100 parts by weight of the monomer mixture. If the dispersion stabilizing agent is used in an amount of more than 20 parts by weight, the suspension may exhibit so high a viscosity that the suspension cannot flow. On the other hand, if the dispersion stabilizing agent is used in an amount of less than 0.1 parts by weight, the porous resin particles may not be sufficiently dispersed and stick together.

The suspension polymerization may be carried out in the presence of a surfactant to further stabilize the suspension (reaction liquid). For example, a surfactant may be further added to an aqueous phase containing the aqueous medium or to the mixture (oil phase) containing the monomer mixture and the organic solvent. The surfactant may be anionic, cationic, nonionic, or zwitterionic.

Examples of anionic surfactants include sodium oleate; potassium soap of castor oils, such as fatty acid soap; alkyl sulfate salts, such as sodium lauryl sulfate and ammonium lauryl sulfate; alkylbenzene sulfonates, such as sodium dodecylbenzenesulfonate; alkyl naphthalene sulfonates; alkane sulfonates; dialkyl sulfosuccinates, such as sodium dioctyl sulfosuccinate; alkenyl succinates (dipotassium salt); alkyl phosphate salts; naphthalenesulfonate formaldehyde condensates; polyoxyethylene alkyl ether sulfate salts, such as polyoxyethylene alkylphenyl ether sulfate salt and sodium polyoxyethylene lauryl ether sulfate; and polyoxyethylene alkyl sulfate salts.

Examples of nonionic surfactants include polyoxyethylene alkyl ethers, polyoxyethylene alkylphenyl ethers, polyoxyethylene fatty acid esters, sorbitan fatty acid esters, polyoxysorbitan fatty acid esters, polyoxyethylene alkylamine, glycerol fatty acid esters, and oxyethylene-oxypropylene block polymers.

Examples of cationic surfactants include alkylamine salts, such as lauryl amine acetate and stearyl amine acetate; and quaternary ammonium salts, such as lauryl trimethylammonium chloride.

Examples of zwitterionic surfactants include lauryl dimethylamine oxides, betaine lauryl dimethylamino acetates, phosphate ester-based surfactants, and phosphite ester-based surfactants.

Any one of the surfactants may be used alone; alternatively, two or more of them may be used in any combination. One can select a surfactant and adjust its amount in a suitable manner, in view of the stability of dispersion of the monomer mixture during the suspension polymerization.

The polymerization temperature for the monomer mixture is preferably from 40° C. up to a temperature that is equal to the boiling point T° C. of the organic solvent minus 5° C. The polymerization temperature is maintained for preferably 0.1 hours to 20 hours. When the polymerization is completed, a suspension (slurry) is obtained that contains porous resin particles containing the organic solvent. The organic solvent contained in the suspension is removed in the distillation step (which will be described later in detail).

If the suspension polymerization is carried out in the polymerization step after oil phase droplets containing the monomer mixture are dispersed in the aqueous phase using, for example, a high-pressure disperser, such as a microfluidizer or a nanomizer, that exploits collisions between droplets and impact of collision onto a machine wall, the resultant porous resin particles have consistent particle diameters.

Distillation Step

The suspension containing the porous resin particles prepared in the polymerization step is distilled in the distillation step to remove the organic solvent from the suspension.

In the distillation step, for example, the suspension containing the porous resin particles prepared in the polymerization step is introduced into a still. Distillation is then carried out while stirring at a temperature and pressure at which at least the organic solvent can be distilled.

Distillation conditions may vary depending on the type of organic solvent used in the polymerization step. Typically, distillation is preferably carried out at a temperature higher than or equal to the boiling point of the organic solvent and under reduced pressure of less than or equal to 0.030 MPa.

The distillation step carried out as above removes the organic solvent from the suspension and may further remove the polymerization initiator and the residue of the polymerization initiator contained in the suspension and the residual, unreacted monomer in the suspension (specifically, monofunctional (meth)acrylic acid ester and crosslinking monomer).

Decomposition and Removal Step

If a dispersion stabilizing agent is used in the polymerization step, the dispersion stabilizing agent contained in the suspension is preferably decomposed and removed after the distillation step. For example, if a dispersion stabilizing agent that decomposes in acid and dissolve in water is used in the polymerization step, the dispersion stabilizing agent may be decomposed and removed by adding acid to the suspension from which the organic solvent has been removed in the distillation step to decompose and dissolve the dispersion stabilizing agent in the suspension, subsequently filtering the suspension to filter out the porous resin particles, and washing the filtered-out porous resin particles in water.

The decomposition and removal step carried out as above reduces the amount of residual metal that originally comes from the dispersion stabilizing agent contained in the porous resin particles manufactured by the method of manufacturing porous resin particles of the present invention.

Drying Step

After the distillation step (if a decomposition and removal step is carried out, then after that decomposition and removal step), the porous resin particles filtered out from the suspension are preferably dried as detailed below.

The porous resin particles filtered out from the suspension are dried under reduced pressure of less than or equal to 0.015 MPa, preferably of less than or equal to 0.010 MPa, at a temperature higher than or equal to 70° C. and lower than or equal to 90° C. for 12 hours or longer, more preferably 15 hours or longer.

The drying step carried out as above reduces the polymerization initiator and the residue of the polymerization initiator contained in the porous resin particles and the residual monomer in the porous resin particles (specifically, monofunctional (meth)acrylic acid ester and crosslinking monomer).

External Preparation

The external preparation of the present invention contains the porous resin particles of the present invention. The external preparation of the present invention contains the porous resin particles of the present invention that have excellent light diffusion and oil absorbing properties. Therefore, the external preparation, when applied to the skin, absorbs sebum to make the skin smooth and reduce glaring and makes skin pores, colored skin spots, and wrinkles less visually recognizable by multiple light scattering (light diffusion). If the external preparation of the present invention contains the porous resin particles of the present invention with a low bulk specific gravity, the external preparation exhibits excellent spreadability when applied to the skin.

The amount of porous resin particles in the external preparation of the present invention may be specified in a suitable manner according to the type of the external preparation. The amount is preferably 1 wt % to 80 wt % and more preferably 3 wt % to 70 wt %. If the porous resin particles account for less than 1 wt % of the entire external preparation, the porous resin particles may fail to exhibit appreciable effect. If the porous resin particles account for more than 80 wt %, the extra amount may fail to produce worthwhile appreciable effect, which is not desirable in terms of manufacturing cost.

The external preparation of the present invention may be used, for example, as external medicines and cosmetic preparations. The external medicines are by no means limited in any particular manner, provided that they are applicable to the skin. Specific examples include skin creams, ointments, and emulsions. Examples of cosmetic preparations include cleaning cosmetics, such as soaps, body shampoos, face washing creams, scrub cleansers, and toothpastes; makeup preparations, such as makeup powders, face powders (loose powders, breast powders, etc.), makeup foundations (powder makeup foundations, liquid makeup foundations, emulsion makeup foundations, etc.), lipsticks, lip balms, cheek colors, eye makeup cosmetics (eye shadows, eyeliners, mascara, etc.), and nail polishes; lotion preparations, such as pre-shave lotions and body lotions; external preparations for body, such as body powders and baby powders; skin care preparations, such as cosmetic lotions, skin creams, and milky lotions (makeup milky lotions); antiperspirants (liquid antiperspirants, solid antiperspirants, creamy antiperspirants, etc.); skin packs; hair washing cosmetics; hair coloring preparations; hair dressings; fragrances; bath preparations; sun screen products; suntan products; and shaving creams.

The porous resin particles of the present invention are preferably used for, among the examples above, cosmetic preparations in powder form (in other words, powder cosmetic preparations), such as makeup powders, face powders, powder makeup foundations, body powders, and baby powders because the particles provide external preparations with an excellent oil absorbing property.

The porous resin particles compounded into the external preparation of the present invention may be treated with a surface treatment agent (e.g., an oil material, silicone compound, or fluorine compound), organic powder, or inorganic powder.

The oil material is by no means limited in any particular manner, provided that it is generally used with external preparations. Examples include hydrocarbon oils, such as liquid paraffins, squalane, petrolatums, paraffin waxes; higher fatty acids, such as lauric acid, myristic acid, palmitic acid, stearic acid, oleic acid, behenic acid, undecylenic acid, oxystearic acid, linoleic acid, lanolin fatty acid, and synthetic fatty acids; ester oils, such as glyceryl trioctanoate, propylene glycol dicaprate, cetyl 2-ethyl hexanoate, and isocetyl stearate; waxes, such as beeswax, spermaceti, lanolin, carnauba wax, and candelilla wax; oils and fats, such as linseed oil, cottonseed oil, castor oil, egg-yolk oil, and coconut oil; metal soaps, such as zinc stearate and zinc laurate; and higher alcohols, such as cetyl alcohol, stearyl alcohol, and oleyl alcohol. The method by which the porous resin particles are treated with an oil material is by no means limited in any particular manner. Typical examples include dry and wet methods. A dry method adds an oil material to the porous resin particles and stirs the mixture with, for example, a mixer to coat the porous resin particles with the oil material. A wet method dissolves an oil material in ethanol, propanol, ethyl acetate, hexane, or another suitable solvent under heat, adds the porous resin particles to the dissolved oil material, mixes and stirs them, and subsequently removes the solvent under reduced pressure or heat, to coat the porous resin particles with the oil material.

The silicone compound is by no means limited in any particular manner, provided that it is generally used with external preparations. Examples include dimethyl polysiloxane, methyl hydrogen polysiloxane, methylphenyl polysiloxane, acrylic-silicone-based graft polymers, organic silicone resins, and partially crosslinked organopolysiloxane polymers. The method by which the porous resin particles are treated with a silicone compound is by no means limited in any particular manner. Examples include the aforementioned dry and wet methods. An additional baking process may be carried out where necessary, and/or when a reactive silicone compound is used, a reaction catalyst, as an example, may be added in a suitable manner.

The fluorine compound is by no means limited in any particular manner, provided that it can be generally compounded into external preparations. Examples include perfluoro-alkyl-group-containing esters, perfluoro alkyl silane, perfluoropolyethers, and perfluoro-group-containing polymers. The method by which the porous resin particles are treated with a fluorine compound is by no means limited in any particular manner. Examples include the aforementioned dry and wet methods. An additional baking process may be carried out where necessary, and/or when a reactive fluorine compound is used, a reaction catalyst, as an example, may be added in a suitable manner.

Examples of the organic powder include natural macromolecular compounds, such as gum arabic, gum tragacanth, guar gum, locust bean gum, karaya gum, Irish moss, Quince seed, gelatin, shellac, rosin, and casein; semisynthetic macromolecular compounds, such as sodium carboxymethyl cellulose, hydroxyethyl cellulose, methyl cellulose, ethyl cellulose, sodium alginate, gum ester, nitrocellulose, hydroxypropyl cellulose, and crystalline cellulose; polyvinyl alcohols; polyvinylpyrrolidone; sodium polyacrylate; carboxyvinyl polymers; polyvinyl methyl ethers; polyamide resins; silicone oil; and resin particles, such as nylon particles, polymethyl methacrylate particles, crosslinked polystyrene particles, silicone particles, urethane particles, polyethylene particles, and fluorine resin particles. Examples of the inorganic powder include iron oxides, ultramarines, ferric ferrocyanide, chromium oxides, chromium hydroxide, carbon black, manganese violet, titanium oxide, zinc oxide, talc, kaolin, mica, calcium carbonate, magnesium carbonate, isinglass, aluminum silicate, barium silicate, calcium silicate, magnesium silicate, silica, zeolite, barium sulfate, calcined calcium sulfate (calcined gypsum), calcium phosphate, hydroxyapatite, and ceramic powder. These organic and inorganic powders may be surface-treated in advance. Examples of the surface treatment method include the aforementioned publicly known surface treatment techniques.

Commonly used main agents or additives may be compounded into the external preparation of the present invention where necessary as long as they do not impair the effects of the present invention. Examples of such main agents and additives include water, lower alcohol (alcohols with 5 or fewer carbon atoms), oils, fats and waxes, hydrocarbons, higher fatty acids, higher alcohols, sterols, fatty acid esters, metal soaps, moisturizing agents, surfactants, macromolecular compounds, color material ingredients, fragrances, clay minerals, antiseptics, anti-inflammatory agents, antioxidants, ultraviolet light absorbers, organic-inorganic composite particles, pH adjusters (e.g., triethanol amine), specially compounded additives, and pharmaceutical active ingredients.

Concrete examples of oils, fats, and waxes include avocado oil, almond oil, olive oil, cacao butter, beef tallow, sesame oil, wheat germ oil, safflower oil, shea butter, turtle oil, camellia oil, persic oil, castor oil, grape seed oil, macadamia nut oil, mink oil, egg-yolk oil, Japan wax, coconut oil, rose hip oil, hardened oil, silicone oil, orange roughy oil, carnauba wax, candelilla wax, spermaceti, jojoba oil, montan oil, beeswax, and lanolin.

Concrete examples of hydrocarbons include liquid paraffins, petrolatums, paraffins, ceresins, microcrystalline waxes, and squalane.

Concrete examples of higher fatty acid include fatty acids with 11 or more carbon atoms, such as lauric acid, myristic acid, palmitic acid, stearic acid, oleic acid, behenic acid, undecylenic acid, oxystearic acid, linoleic acid, lanolin fatty acid, and synthetic fatty acid.

Concrete examples of higher alcohols include alcohols with 6 or more carbon atoms, such as lauryl alcohol, cetyl alcohol, cetostearyl alcohol, stearyl alcohol, oleyl alcohol, behenyl alcohol, lanolin alcohol, hydrogenated lanolin alcohol, hexyldecanol, octyldecanol, isostearyl alcohol, jojoba alcohol, and decyltetradecanol.

Concrete examples of sterols include cholesterol, dihydrocholesterol, and phytocholesterol.

Concrete examples of fatty acid esters include linoleic acid esters, such as ethyl linoleate; lanolin fatty acid esters, such as lanolin fatty acid isopropyl; lauric acid esters, such as hexyl laurate; myristic acid esters, such as isopropyl myristate, myristyl myristate, cetyl myristate, octyldecyl myristate, and octyldodecyl myristate; oleic acid esters, such as decyl oleate and octyldodecyl oleate; dimethyl octanoic acid esters, such as hexyldecyl dimethyloctanoate; isooctanoic acid esters, such as cetyl isooctanoate (cetyl 2-ethyl hexanoate); palmitic acid esters, such as decyl palmitate; and cyclic alcohol fatty acid esters, such as glycerin trimyristate, glycerin tri(capryl caprate), propylene glycol dioleate, glycerin triisostearate, glycerin triisooctanoate, cetyl lactate, myristyl lactate, diisostearyl malate, cholesteryl isostearate, and cholesteryl 12-hydroxystearate.

Concrete examples of metal soaps include zinc laurate, zinc myristate, magnesium myristate, zinc palmitate, zinc stearate, aluminum stearate, calcium stearate, magnesium stearate, and zinc undecylenate.

Concrete examples of moisturizing agents include glycerin, propylene glycol, 1,3-butylene glycol, polyethylene glycol, sodium dl-pyrrolidonecarboxylate, sodium lactate, sorbitol, sodium hyaluronate, polyglycerin, xylitol, and maltitol.

Concrete examples of surfactants include anionic surfactants, such as higher fatty acid soaps, higher alcohol sulfuric acid esters, N-acyl glutamic acid salts, and phosphoric acid ester salts; cationic surfactants, such as amine salts and quaternary ammonium salts; amphoteric surfactants, such as betaine surfactants, amino acid surfactants, imidazoline surfactants, and lecithin; and nonionic surfactants, such as fatty acid monoglyceride, polyethylene glycol, propylene glycol fatty acid esters, sorbitan fatty acid esters (e.g., sorbitan isostearate), sucrose fatty acid esters, polyglycerol fatty acid esters, and ethylene/oxide condensates.

Concrete examples of macromolecular compounds include natural macromolecular compounds, such as gum arabic, gum tragacanth, guar gum, locust bean gum, karaya gum, Irish moss, Quince seed, gelatin, shellac, rosin, and casein; semisynthetic macromolecular compounds, such as sodium carboxymethyl cellulose, hydroxyethyl cellulose, methyl cellulose, ethyl cellulose, sodium alginate, gum ester, nitrocellulose, hydroxypropyl cellulose, and crystalline cellulose; and synthetic macromolecular compounds, such as polyvinyl alcohols, polyvinylpyrrolidone, sodium polyacrylate, carboxyvinyl polymers, polyvinyl methyl ethers, polyamide resins, silicone oil, nylon particles, poly (meth)acrylic acid ester particles (e.g., poly(methyl methacrylate) particles), polystyrene particles, silicone-based particles, urethane particles, polyethylene particles, silica particles, and other resin particles.

Concrete examples of color material ingredients include inorganic pigments, such as iron oxides (red iron oxide, yellow iron oxide, black iron oxide), ultramarines, ferric ferrocyanide, chromium oxides, chromium hydroxide, carbon black, manganese violet, titanium oxide, zinc oxide, talc, kaolin, calcium carbonate, magnesium carbonate, isinglass, aluminum silicate, barium silicate, calcium silicate, magnesium silicate, silica, zeolite, barium sulfate, calcined calcium sulfate (calcined gypsum), calcium phosphate, hydroxyapatite, and ceramic powder; and tar dyes, such as azo-, nitro-, nitroso-, xanthene-, quinoline-, anthraquinoline-, indigo-, triphenylmethane-, phthalocyanine-, and pyrene-based dyes.

The powder ingredients for the macromolecular compounds and for the color material ingredients may be subjected to a surface treatment before use. The surface treatment may be carried out by any publicly known surface treatment technique. Examples include treatment with an oil material, such as hydrocarbon oil, ester oil, or lanolin; treatment with silicone, such as dimethyl polysiloxane, methyl hydrogen polysiloxane, or methylphenyl polysiloxane; treatment with a fluorine compound, such as a perfluoro-alkyl-group-containing ester, perfluoro alkyl silane, a perfluoropolyether, and a perfluoro-alkyl-group-containing polymer; treatment with a silane coupling agent, such as 3-methacryloxypropyltrimethoxy silane or 3-glycidoxypropyltrimethoxy silane; treatment with a titanium coupling agent, such as isopropyltriisostearoyl titanate or isopropyl tris(dioctyl pyrophosphate) titanate; treatment with a metal soap; treatment with an amino acid, such as acyl glutamic acid; treatment with a lecithin, such as hydrogenated egg-yolk lecithin; treatment with collagen; treatment with polyethylene; moisturizing treatment; treatment with an inorganic compound; and mechanochemical treatment.

Concrete examples of clay minerals include components that have several functions (e.g., capable of acting as an extender pigment and an adsorbent), such as talc, mica, sericite, titanium sericite (sericite coated with titanium oxide), white isinglass, and VEEGUM® manufactured by R.T. Vanderbilt Company, Inc.

Concrete examples of fragrances include anisaldehyde, benzyl acetate, and geraniol. Concrete examples of antiseptics include methyl parapen, ethyl parapen, propyl parapen, benzalkonium, and benzethonium. Concrete examples of antioxidants include dibutylhydroxytoluene, butylhydroxyanisole, propyl gallate, and tocopherol. Concrete examples of ultraviolet light absorbers include inorganic absorbers (e.g., fine particles of titanium oxide, zinc oxide, cerium oxide, iron oxide, and zirconium oxide) and organic absorbers (e.g., benzoic acid-based, para-aminobenzoic acid-based, anthranilic acid-based, salicylic acid-based, cinnamic acid-based, benzophenone-based, and dibenzoylmethane-based absorbers).

Concrete examples of the specially compounded additive include hormones, such as estradiol, estrone, ethinylestradiol, cortisone, hydrocortisone, and prednisone; vitamins, such as vitamin A, vitamin B, vitamin C, and vitamin E; skin astringents, such as citric acid, tartaric acid, lactic acid, aluminum chloride, aluminum potassium sulfate, allantoin chlorohydroxy aluminum, zinc para-phenolsulfonate, and zinc sulfate; trichogenous accelerants, such as cantharides tincture, capsicum tincture, ginger tincture, swertia extract, garlic extract, hinokitiol, carpronium chloride, glyceride pentadecanate, vitamin E, estrogen, and photosensitive elements; and whitening agents, such as magnesium L-ascorbyl-phosphate and kojic acid.

Coating Agent

The porous resin particles of the present invention may be contained, for example, as a coating film softening agent, a coating material flatting agent, or a light diffusion agent in a coating agent. The coating agent of the present invention contains the porous resin particles of the present invention.

The coating agent may contain a binder resin where necessary. The binder resin is either a resin soluble in an organic solvent or water or an emulsion-type aqueous resin dispersible in water as examples, and may be any publicly known binder resin. Specific examples of the binder resin include acrylic resins, such as Dianal® LR-102 and Dianal® BR-106 (trade names) manufactured by Mitsubishi Rayon Co., Ltd. and Medium VM(K) (trade name) manufactured by Dainichiseika Color & Chemicals Mfg. Co., Ltd.; alkyd resins; polyester resins; polyurethane resins; chlorinated polyolefin resins; and amorphous polyolefin resins. Any one of these binder resins may be selected as needed according to environmental and other conditions for use, including adhesiveness of the coating material to the base material to be coated.

The porous resin particles may be compounded in an amount that is adjustable in a suitable manner, for example, according to the thickness of the coating film to be formed by a coating agent containing the binder resin, the average particle diameter of the porous resin particles, the coating method, and applications and preferably in an amount of 1 part by weight to 300 parts by weight per 100 parts by weight of the binder. The porous resin particles are compounded in an amount of more preferably 5 wt % to 50 wt % and even more preferably 8 wt % to 40 wt % of the sum of the binder resin (solid equivalent if an emulsion-type aqueous resin is used) and the porous resin particles. If the porous resin particles account for less than 5 wt %, sufficient matting effect may not be obtained. On the other hand, if the porous resin particles account for more than 50 wt %, the coating agent may have so high a viscosity that the porous resin particles could not disperse properly, which would cause microcracks on the surface of the coating film formed by coating with the coating agent, roughness of the surface of the coating film, and other external aesthetic defects on the surface of the coating film.

The coating agent may contain a medium where necessary. The medium is preferably a solvent that dissolves the binder resin or a dispersion medium that disperses the binder resin. The dispersion medium and the solvent may be either aqueous or oily. Examples of oily mediums include hydrocarbon-based solvents, such as toluene and xylene; ketone-based solvents, such as methyl ethyl ketones and methyl isobutyl ketones; ester-based solvents, such as ethyl acetate and butyl acetate; and ether-based solvents, such as dioxane, ethylene glycol diethyl ether, and ethylene glycol monobutyl ether. Examples of aqueous media include water and alcohols (e.g., isopropanol). Any one of these solvents may be used alone; alternatively, two or more of them may be mixed for use. The medium typically accounts for 20 wt % to 60 wt % of the total amount of the coating agent.

The coating agent may further contain other additives, such as curing agents, coloring agents (extender pigments, coloring pigments, metal pigments, mica powder pigments, dyes, etc.), antistatic agents, leveling agents, fluidity adjusters, ultraviolet light absorbers, and light stabilizers.

The base material to be coated with the coating agent is by no means limited in any particular manner and may be any base material suitable for use.

For example, in optical applications, the base material may be, for example, a transparent base material, such as a glass base material or a transparent base resin. Optical films, such as light diffusion films and anti-glare films, may be manufactured by using a transparent base material as the base material and coating the transparent base material with a coating agent that contains no coloring agent (coating agent for light diffusion) to form a transparent coating film. When this is the case, the porous resin particles act as a light diffusion agent.

Matting paper may be manufactured by using paper as the base material and applying a coating agent that contains no coloring agent (paper coating agent) to form a transparent coating film.

The method by which the coating agent is applied is by no means limited in any particular manner and may be any publicly known method. The coating agent may be applied, for example, by spray coating, roll coating, brush coating, or another like method. The coating agent may be diluted with a diluent to adjust its viscosity as necessary. Examples of the diluent include hydrocarbon-based solvents, such as toluene and xylene; ketone-based solvents, such as methyl ethyl ketones and methyl isobutyl ketones; ester-based solvents, such as ethyl acetate and butyl acetate; ether-based solvents, such as dioxane and ethylene glycol diethyl ether; water; and alcohol-based solvents. Any one of these diluents may be used alone; alternatively, two or more of them may be mixed for use. To manufacture an optical film, the coating/application method is preferably such that irregularities are formed on the surface of the coating film by the porous resin particles.

Optical Film

The optical film of the present invention is the coating agent of the present invention applied to a base material. Concrete examples of the optical film include diffusion films and anti-glare films.

Concrete examples of base materials for the optical film include glass base materials and transparent base materials containing a transparent base resin.

Examples of the transparent base resin include polyesters, polyethylenes, polypropylenes, and polystyrenes, such as acrylic resins, alkyl (meth)acrylate/styrene copolymers, polycarbonates, and polyethylene terephthalates (hereinafter, abbreviated "PETs"). Among these transparent base resins, acrylic resins, alkyl (meth)acrylate/styrene copolymers, polycarbonates, polyesters, and polystyrenes are preferred if the transparent base resin is required to exhibit excellent transparence. Any one of these transparent base resins may be used alone; alternatively, two or more of them may be used in any combination.

Resin Compositions

The resin composition of the present invention contains a base resin and the porous resin particles of the present invention. The resin particle composition of the present invention contains the porous resin particles of the present invention and exhibits excellent light diffusion properties. Therefore, the resin composition of the present invention may be used as an ingredient for light diffusion members (light diffusers), such as lighting covers (lighting covers for light-emitting diodes (LED), lighting covers for fluorescent tubes, etc.), light diffusion sheets, and light diffusion plates.

The base resin is typically a different thermoplastic resin from the components of a polymer constituting the porous resin particles. Examples of thermoplastic resins used as the base resin include acrylic resins, alkyl (meth)acrylate/styrene copolymers, polycarbonates, polyesters, polyethylenes, polypropylenes, and polystyrenes. Among these thermoplastic resins, acrylic resins, alkyl (meth)acrylate/styrene copolymers, polycarbonates, polyesters, and polystyrenes are preferred if the base resin is required to exhibit excellent transparence. Any one of these thermoplastic resins may be used alone; alternatively, two or more of them may be used in any combination.

The proportion of added porous resin particles to the base resin is preferably 1 part by weight to 300 parts by weight, more preferably 10 parts by weight to 100 parts by weight, per 100 parts by weight of the base resin. If the porous resin particles are less than 1 part by weight, the porous resin particles may hardly impart light diffusion properties to the light diffusion member. If the porous resin particles are more than 300 parts by weight, the porous resin particles do impart light diffusion properties to the light diffusion member, but may cause excessively low optical transparency in the light diffusion member.

The resin composition may be manufactured by a method that is by no means limited in any particular manner. For example, the resin composition may be manufactured by mixing porous resin particles and a base resin by a mechanical pulverization/mixing or any other like publicly known conventional method. In mechanical pulverization/mixing, the porous resin particles are mixed and stirred with the base resin using a device, such as a Henschel mixer, a V-type mixer, a Turbula mixer, a hybridizer, or a rocking mixer, to manufacture the resin composition.

Molded Object

A molded object of the present invention is obtained by molding a resin composition of the present invention. Concrete examples of the molded object of the present invention include light diffusion members, such as lighting covers (e.g., lighting covers for light-emitting diode (LED) illumination and lighting covers for fluorescent tube illumination), light diffusion sheets, and light diffusion plates.

Molded objects of any given shape may be obtained by, for example, mixing porous resin particles and a base resin in a mixer, kneading with a melt-kneader, such as an extruder, to prepare pellets of a resin composition, and subsequently either extrusion-molding or melting and injection-molding those pellets.

EXAMPLES OF THE INVENTION

The following will specifically describe the present invention by way of examples and comparative examples. The present invention is however by no means limited by these examples.

First will be described a method of measuring the volume-average particle diameter of resin particles, a method of measuring the specific surface area of resin particles, a method of measuring the pore diameter and volume of resin particles, a method of measuring the bulk specific gravity of resin particles, a method of measuring the oil absorption amount of resin particles, a method of measuring the compression strength of resin particles, a method of evaluating the light diffusion properties of resin particles, a method of measuring the amount of residual alkyl methacrylate, and a sensory test on resin particles, all used in the examples and comparative examples.

Method of Measuring Volume-Average Particle Diameter of Resin Particles

The volume-average particle diameter of resin particles was measured with a Coulter Multisizer III (measuring instrument manufactured by Beckman Coulter, Inc.) by using the apertures calibrated according to the User's Manual for Multisizer™ 3 published by Beckman Coulter, Inc.

The apertures to be used for the measurement were selected in a suitable manner. For example, 50-μm apertures were selected if the resin particles to be measured had a predicted volume-average particle diameter of greater than or equal to 1 μm and less than or equal to 10 μm; 100-μm apertures were selected if the resin particles to be measured had a predicted volume-average particle diameter of greater than 10 μm and less than or equal to 30 μm; 280-μm apertures were selected if the resin particles had a predicted volume-average particle diameter of greater than 30 μm and less than or equal to 90 μm; and 400-μm apertures were selected if the resin particles had a predicted volume-average particle diameter of greater than 90 μm and less than or equal to 150 μm. If the measured volume-average particle diameter differed from the predicted volume-average particle diameter, the apertures were replaced with those with a proper size for another measurement.

When 50-μm apertures were selected, the aperture current was set to −800, and the gain was set to 4; when 100-μm apertures were selected, the aperture current was set to −1,600, and the gain was set to 2; and when 280 μm or 400-μm apertures were selected, the aperture current was set to −3,200, and the gain was set to 1.

Measurement samples were dispersion liquids prepared by dispersing 0.1 g of resin particles in 10 ml of a 0.1 wt % aqueous solution of a nonionic surfactant using a touch mixer ("TOUCHMIXER MT-31" manufactured by Yamato Scientific Co., Ltd.) and an ultrasonic cleaner ("ULTRASONIC CLEANER VS-150" manufactured by Velvo-Clear). A beaker was filled with ISOTON® II (electrolyte solution for use in measurement manufactured by Beckman Coulter, Inc.) and placed in the measuring unit of the Coulter Multisizer III. The dispersion liquid was added dropwise while gently stirring the content of the beaker. Densitometer readings on the screen of the main body of the Coulter Multisizer III were adjusted to 5 to 10% before measurement was started. The content of the beaker was stirred so gently as to prevent cells from forming during measurement. The measurement was finished when 100,000 particles were measured.

The volume-average particle diameter is an arithmetic average in the volume-based particle size distribution of 100,000 particles.

Method of Measuring Specific Surface Area of Resin Particles

The specific surface area of resin particles was measured by BET (nitrogen adsorption method) stipulated in ISO 9277, 1$^{st}$ Ed., JIS Z 8830: 2001. A BET nitrogen adsorption isotherm for target resin particles was obtained by measurement using an automatic specific surface area/fine pore distribution measuring instrument Tristar3000 manufactured by Shimadzu Corporation. The specific surface area was calculated from the amount of adsorbed nitrogen by multi-point BET. Pre-treatment was carried out by hot gas purge. After that, measurement was carried out by a constant-volume method using nitrogen as the adsorbate under a condition where the cross-sectional area of the adsorbate was 0.162 nm$^2$. The pre-treatment was carried out specifically by nitrogen-purging for 20 minutes while heating resin particles in a container at 65° C., letting them cool down at room temperature, subsequently deaerating in a vacuum, while heating them at 65° C., until the pressure inside the container reached less than or equal to 0.05 mmHg.

Method of Measuring Pore Diameter and Pore Volume of Resin Particles

The pore diameter (average pore diameter) and pore volume of the pores of resin particles were determined by BJH. A nitrogen desorption isotherm for target resin particles to be measured was obtained by measurement using an automatic specific surface area/fine pore distribution measuring instrument Tristar3000 manufactured by Shimadzu Corporation. The pore diameter (average pore diameter) and pore volume (integral pore volume) were calculated based on BJH. The nitrogen desorption isotherm was obtained by a constant-volume method using nitrogen as the adsorbate under a condition where the cross-sectional area of the adsorbate was 0.162 $nm^2$.

Method of Measuring Bulk Specific Gravity of Resin Particles

The bulk specific gravity (packed apparent specific gravity) of resin particles was measured using a PT-E powder tester manufactured by Hosokawa Micron Corporation. Specifically, accessories (fixed chute, vibrating chute, space ring, sieve with 710-μm openings, sieve holder) were attached to the main body of the PT-E powder tester. A rectangular putt was placed under the accessories. A cup (capacity: 100 mL), an accessory for the main body of the PT-E powder tester, was placed in a recess in the cup base of the table. Thereafter, a proper amount of resin particles to be measured was gently placed on the sieve using a scoop (another accessory for the PT-E powder tester). The sieve was shaken until the cup (capacity: 100 mL) was filled (which took 20 seconds to 30 seconds). Next, a cap (another accessory for the PT-E powder tester) was connected to the top of the cup, and additional resin particles were gently put to the top of the cap. The cup was then placed in a tapping holder. A cap cover was attached onto the cap to prevent the resin particles inside the cup from bouncing during tapping. After tapping for 180 seconds (60 times/min.), excess resin particles were removed from the top of the cup using a vertically erected blade (another accessory for the PT-E powder tester), leaving exactly a level cup of resin particles. The resin particles were weighed in an even balance. The bulk specific gravity (packed apparent specific gravity) was then calculated from the weight (g) of the resin particles according to the equation:

Bulk Specific Gravity (g/mL)=Weight (g) of Resin Particles/100 mL

Method of Measuring Oil Absorption Amount for Resin Particles

The oil absorption amount for resin particles was measured by a modified JIS K 510113-2 measuring method. Purified linseed oil was used in place of boiled linseed oil, and a new criterion was used to determine an end point. Details of the measurement of oil absorption amounts follow.

(A) Devices and Tools

Measurement plate: flat and smooth glass plate with dimensions greater than 300 mm×400 mm×5 mm Palette knife (spatula): Steel or stainless steel blade with handle Chemical balance (weighing scales): Capable of measuring down to order of 10 mg Burette: 10-mL capacity as specified in JIS R 3505

(B) Reagent

Purified linseed oil: As specified in ISO 150 (first-grade linseed oil manufactured by Wako Pure Chemical Industries Ltd. was used)

(C) Measuring Method (1) Resin particles (1 g) were placed at the center of a measurement plate. Four or five droplets of purified linseed oil were slowly added at a time from the burette to the center of the resin particles. Every time droplets were added, both the resin particles and the purified linseed oil were thoroughly kneaded with a palette knife.

(2) The dropwise addition and kneading were repeated until the whole resin particles and the purified linseed oil formed a hard putty-like mass. After that, one droplet of purified linseed oil was added at a time, and the whole mixture was kneaded. An end point was regarded as having been reached when the addition of one droplet of purified linseed oil abruptly softened the paste (kneaded article of resin particles and purified linseed oil) so that the paste started to flow.

(3) Determining Flow

The paste was determined to have flown if the addition of a droplet of purified linseed oil abruptly softened the paste so that the paste moved when the measurement plate was erected upright. If the paste did not move on the vertically erected measurement plate, another droplet of purified linseed oil was added.

(4) The amount of purified linseed oil consumed up to the end point, as indicated by the decrease in the amount of the liquid in the burette, was read off the burette.

(5) Each measurement was completed within 7 to 15 minutes. If the measurement lasted longer than 15 minutes, the measurement was started all over again. Only those results from measurements that were completed within the specified period were accepted.

(D) Calculating Oil Absorption Amount

The oil absorption amount per 100 g of the sample was calculated using the following equation:

$O=(V/m)\times 100$ where O is an oil absorption amount (mL/100 g), m is the weight of resin particles (g), and V is the volume of consumed purified linseed oil (mL).

Method of Measuring Compression Strength of Resin Particles

The compression strength (S10 strength) of resin particles was measured using a micro compression testing machine "MCTM-200" manufactured by Shimadzu Corporation under the following conditions.

Specifically, a dispersion liquid containing ethanol in which resin particles were dispersed was applied onto a mirror-finished steel sample table and dried to prepare measurement samples. Next, a single, independent fine resin particle (no other resin particles were present at least within a diameter of 100 μm) was selected under the optical microscope of the MCTM-200 at room temperature (20° C.) and a relative humidity of 65%. The diameter of the selected resin particle was measured using the particle diameter measuring cursor of the MCTM-200. A fine particle with a diameter of 6 μm to 12 μm was selected, and no resin particles with a diameter outside this range were used in measuring the compression strength. Next, the selected resin particle was placed under a load which was increased gradually up to a maximum load of 9.81 mN by lowering the testing indenter onto the top of the resin particle at the load velocity below. The compression strength was determined using the following equation from the load under which the pre-measured diameter of the resin particle decreased by 10%. Each resin particle was measured six times. Results of four measurements, excluding the maximum and minimum values, were averaged as the compression strength (S10 strength) when compressed by 10%.

Equation for Calculation of Compression Strength

Compression Strength (MPa)=2.8×Load(N)/{π×(Particle Diameter (mm))$^2$}

Conditions Under which Compression Strength was Measured

Temperature: Normal temperature (20° C.), relative humidity 65%

Upper Press Indenter: Flat indenter (made of diamond) with 50-μm diameter

Lower Press Plate: SKS flat plate

Test Type: Compression test (MODE1)

Test Load: 9.81 mN

Load Velocity: 0.732 mN/sec

Maximum Depression; 20 (μm)

Method of Evaluating Light Diffusion Properties of Resin Particles

The diffusibility of light reflected off the resin particle surface was evaluated by the following method.

Measuring Reflection Luminous Intensity Distribution

The reflection luminous intensity distribution of resin particles was measured using a three-dimensional luminous intensity meter (goniophotometer GP-200 manufactured by Murakami Color Research Laboratory) at room temperature (20° C.) and a relative humidity of 65%.

Specifically, the reflection luminous intensity distribution was measured as follows:

(1) A 5 cm×5 cm, square cutout of double-sided adhesive tape (ORT-1 manufactured by Nitto Denko Corporation) 3 was attached, as illustrated in FIG. 1, with the black part of a piece of black and white hiding paper (Test chart 2803 manufactured by BYK-Gardner) 4 being placed at the center.

(2) Next, resin particles 2 were dropped onto an adhesive face of the double-sided adhesive tape 3 placed on the black part of a piece of black and white hiding paper 4 using the funnel and funnel table (JIS K5101-12-1) for an apparent density measuring instrument. After that, excess resin particles 2 on the adhesive face were blown off with 0.05 MPa to 0.1 MPa compressed air.

(3) The black and white hiding paper 4 was placed on a flat glass plate, and another 5 cm×5 cm, square flat glass plate weighing 250 g was placed on the spotting surface of the resin particles 2, to place the resin particles 2 under a load and leave them in that condition for 1 minute. Thereafter, excess resin particles on the adhesive face were blown off again with compressed air.

(4) Steps (2) and (3) were repeated 3 times to obtain a test piece 1 for use in measurement of a reflection luminous intensity distribution. The light reflected off the test piece 1 was measured as follows. As illustrated in FIG. 1, a ray of light 5 from a halogen lamp (light source) was directed to hit the test piece 1 (resin particles 2) at an angle of −45° relative to the normal (0°) of the test piece 1 (resin particles 2). The luminous intensity distribution of rays of light 6 reflected at reflection angles of −90° to +900 were measured using a three-dimensional luminous intensity meter. The position of the test piece 1 was adjusted for the measurement so that the entire incident light could hit the black part of the test piece 1. Reflected light was detected with a photo multiplier tube that had a spectral sensitivity of 185 nm to 850 nm and shows a maximum sensitivity at 530 nm.

Reflected Light Intensity at 0°, +25°, and +75° Relative to Reflected Light Intensity of 100 at +45°

Reflected light intensities (peak luminous intensities) for reflection angles 0°, +25°, and +75° were determined from reflected light intensity data (peak luminous intensity data) for reflection angles 0°, +25°, +45°, and +75° obtained from the measurement of the reflection luminous intensity distribution, with the reflected light intensity (peak luminous intensity) at a reflection angle of +45° being taken as 100. Soft-focus effect, achieved by a cosmetic preparation into which porous resin particles were compounded, grew larger as the reflected light intensities for reflection angles 0°, +25°, and +75° approached 100, with the reflected light intensity for the reflection angle of +45° (specular reflection direction) being taken as 100.

Method of Measuring Amount of Residual Alkyl Methacrylate

The amount of residual, unreacted monofunctional (meth) acrylic acid ester in resin particles may be measured by a publicly known method which could vary depending on the monofunctional (meth)acrylic acid ester used for the manufacture of the resin particles to be measured. Since an alkyl methacrylate, such as methyl methacrylate or ethyl methacrylate, is used as a monofunctional (meth)acrylic acid ester in the examples and comparative examples below, the following will describe a method of measuring the amount of residual, unreacted alkyl methacrylate in resin particles (amount of residual alkyl methacrylate).

(1) Preparing Sample Liquids

One gram of resin particles to be measured, 25 mL of carbon disulfide, and 1 mL of an internal standard liquid were introduced into a test tube and subjected to extraction at room temperature for 12 hours. 1.8 μL of the obtained liquid extract was separated and injected. The internal standard liquid was a mixture of carbon disulfide (75 mL) and toluene (0.1 mL) added to the carbon disulfide.

(2) Measuring Amount of Residual Alkyl Methacrylate

Measurement was carried out on sample liquids using a gas chromatograph (manufactured by Shimadzu Corporation, trade name: "GC-14A") under the conditions below. The amount of alkyl methacrylate (amount of methyl methacrylate, amount of ethyl methacrylate) was quantified by an internal standard method.

Conditions for Measurement

Filling Agent for Column: Liquid phase PEG-20 M

: Carrier Chromosorb W

Column Size: 3 mm I.D.×3,000 mmL

Detector: FID (flame ionization detector)

Carrier Gas: Nitrogen, air, helium

Carrier Gas Flow Rate: 30 mL/min. (nitrogen), 300 mL/min. (air), 35 mL/min. (helium)

Column Temperature: 105° C.

Injection Temperature: 110° C.

Sensory Test for Resin Particles

Powder makeup foundations, emulsion makeup foundations, and body powders containing the resin particles of examples 1 to 6 and comparative examples 1 to 2 below were subjected to a sensory test involving 10 subjects. In the test, powder makeup foundations were evaluated for attributes: soft-focus property, makeup lasting time, spreadability, and softness. Emulsion makeup foundations were evaluated for attributes: soft-focus property, makeup lasting time, and smoothness. Body powders were evaluated for attributes: spreadability and dry feeling. The samples were evaluated for the evaluation attributes on a 4-grade scale using the following criteria.

D . . . Out of 10 subjects, no more than 2 answered that the sample was effective.

C . . . Out of 10 subjects, 3 to 5 answered that the sample was effective.

B . . . Out of 10 subjects, 6 to 8 answered that the sample was effective.

A . . . Out of 10 subjects, no less than 9 answered that the sample was effective.

Example 1

Manufacturing Resin Particles

Magnesium pyrophosphate (80 g) as a dispersion stabilizing agent, 0.25 g of sodium sulfate as an anionic surfactant, and 0.7 g of betaine lauryl dimethylamino acetate (manufactured by NOF Corporation, trade name: Nissananon BL (effective solid content 36 wt %)) as a zwitterionic surfactant were added to 1,200 g of deionized water to prepare an aqueous phase. Meanwhile, a liquid mixture of methyl methacrylate (100 g, or 50 wt % of the whole monomer mixture entire) as a monofunctional (meth)acrylic acid ester, ethylene glycol dimethacrylate (EGDMA) (100 g, or 50 wt % of the whole monomer mixture) as a crosslinking monomer, and ethyl acetate (boiling point: 77° C.) (400 g, or 200 parts by weight per 100 parts by weight of the monomer mixture) as an organic solvent, and 1.8 g of 2,2'-azobis(2, 4-dimethylvaleronitrile) as a polymerization initiator was prepared as an oil phase. The aqueous and oil phases were mixed. Droplets of the oil phase was dispersed in the aqueous phase using a disperser (manufactured by Primix Corporation Co., Ltd., trade name: T. K. homomixer MARK II 2.5) at a rotational speed of 8,000 rpm, to obtain a dispersion liquid. This dispersion liquid was placed in a polymerization vessel equipped with a stirrer and a thermometer. The dispersion liquid was heated to 50° C. while stirring and substituting nitrogen, to initiate suspension polymerization. The internal temperature was maintained at 50° C. for 4 hours and subsequently at 70° C. for 2.5 hours to prepare a suspension containing resin particles (polymerization step).

The suspension containing resin particles was distilled at 70° C. and −0.05 MPa to remove ethyl acetate from the system (distillation step).

Thereafter, the rest of the suspension was cooled down to 20° C. Hydrochloric acid was added to it to decompose magnesium pyrophosphate. After that, the obtained resin particles were filtered out with a Buechner funnel. Subsequently, the resin particles were washed in ion exchanged water (decomposition and removal step).

The washed resin particles were dried at 90° C. and under reduced pressure of 0.008 MPa for 24 hours to obtain resin particles (drying step).

The resin particles obtained in example 1 were porous and had a volume-average particle diameter of 8.2 µm, a specific surface area of 195.5 m$^2$/g, and a bulk specific gravity of 0.385 g/mL.

Manufacturing Powder Makeup Foundation

Starting materials were prepared: the resin particles obtained by the aforementioned manufacture of resin particles (10 parts by weight), talc (42 parts by weight) as a color material ingredient, sericite (17 parts by weight) as a clay mineral, titanium oxide (10 parts by weight) as a color material ingredient, red iron oxide (0.6 parts by weight) as a color material ingredient, yellow iron oxide (1 part by weight) as a color material ingredient, black iron oxide (0.1 parts by weight) as a color material ingredient, a liquid paraffin (2 parts by weight) as a hydrocarbon, octyldecyl myristate (3.5 parts by weight) as a fatty acid ester, sorbitan isostearate (0.5 parts by weight) as a surfactant, and 2-octyl dodecanol (3.0 parts by weight) as a higher alcohol. The resin particles, talc, sericite, titanium oxide, red iron oxide, yellow iron oxide, and black iron oxide were mixed in a Henschel mixer to prepare a mixture. The liquid paraffin, octyldecyl myristate, and sorbitan isostearate were mixed and dissolved in the 2-octyl dodecanol to obtain a solution which was then added to the prepared mixture. The resultant material was then uniformly mixed. This uniform material was pulverized and sieved by publicly known methods to prepare powder. The powder was compression molded in a metal tray by a publicly known method to obtain a powder makeup foundation.

The powder makeup foundation obtained in example 1 had a good makeup lasting time, a high spreadability on the skin, and a soft feel and imparted a high soft-focus property and natural finish to the skin, making the skin look natural.

Manufacturing Emulsion Makeup Foundation

The resin particles obtained by the aforementioned manufacture of resin particles (20.0 parts by weight), sericite (6.0 parts by weight) as a clay mineral, titanium oxide (3.0 parts by weight) as a color material ingredient, and a pigment (suitable amount) were mixed in a Henschel mixer to prepare a powder component.

Separately from the powder component, polyethylene glycol (polyethylene glycol 4000) (5.0 parts by weight), triethanol amine (1.0 parts by weight) as a pH adjuster, propylene glycol (5.0 parts by weight), and VEEGUM® manufactured by R.T. Vanderbilt Company, Inc. (0.5 parts by weight) as a clay mineral were added to purified water (50.2 parts by weight) and dissolved under heat to prepare a solution. The previously prepared powder component was added to this solution. The powder was uniformly dispersed in a homomixer. After that, the solution was maintained at 70° C. to prepare an aqueous phase component.

Next, separately from the aqueous phase component, stearic acid (2.0 parts by weight) as a higher fatty acid, cetyl alcohol (0.3 parts by weight) as a higher alcohol, a liquid paraffin (20.0 parts by weight) as a hydrocarbon, a fragrance (suitable amount), and a preservative (suitable amount) were mixed and dissolved under heat to prepare a solution. After that, the solution was maintained at 70° C. to obtain an oil phase component.

The aqueous phase component was added to the obtained oil phase component, and the resultant mixture was subjected to preliminary emulsification. The mixture was uniformly emulsified and dispersed in a homomixer and cooled down while stirring to obtain an emulsion makeup foundation.

The emulsion makeup foundation obtained in example 1 had a good makeup lasting time and a smooth feel, and imparted a high soft-focus property and natural finish to the skin, making the skin look natural.

Manufacturing Body Powders

The resin particles obtained by the aforementioned manufacture of resin particles (50.0 parts by weight), mica (25.0 parts by weight) as a clay mineral, and sericite (25.0 parts by weight) as a clay mineral were mixed in a Henschel mixer. After that, the mixture was pulverized once using a rotor speed mill ZM-100 manufactured by Retsch (a 12-blade rotor was used, a 1-mm screen was installed, and the rotational speed was set to 14,000 rpm) to obtain body powder.

The body powder obtained in example 1 had a high spreadability on the skin and imparted a dry feeling to the skin.

Example 2

Resin particles were manufactured in the same manner as in example 1, except that the amount of methyl methacrylate used as a monofunctional (meth)acrylic acid ester was changed to 60 g (40 wt % of the whole monomer mixture), the amount of ethylene glycol dimethacrylate (EGDMA) used as a crosslinking monomer was changed to 90 g (60 wt % of the whole monomer mixture), and the amount of ethyl acetate (boiling point 77° C.) used as an organic solvent was changed to 450 g (300 parts by weight per 100 parts by weight of the monomer mixture). From the resin particles thus manufactured, a powder makeup foundation, emulsion makeup foundation, and body powder were manufactured in the same manner as in example 1.

The resin particles obtained in example 2 were porous and had a volume-average particle diameter of 8.0 µm, a specific surface area of 244.7 $m^2/g$, and a bulk specific gravity of 0.306 g/mL.

The powder makeup foundation obtained in example 2 had a good makeup lasting time, a high spreadability on the skin, and a soft feel, and imparted a high soft-focus property and natural finish to the skin, making the skin look natural.

The emulsion makeup foundation obtained in example 2 had a good makeup lasting time and a smooth feel, and imparted a high soft-focus property and natural finish to the skin, making the skin look natural.

The body powder obtained in example 2 had a high spreadability on the skin and imparted a dry feeling to the skin.

Example 3

Resin particles were manufactured in the same manner as in example 1, except that the amount of methyl methacrylate used as a monofunctional (meth)acrylic acid ester was changed to 80 g (40 wt % of the whole monomer mixture), the amount of ethylene glycol dimethacrylate (EGDMA) used as a crosslinking monomer was changed to 120 g (60 wt % of the whole monomer mixture), and the amount of ethyl acetate (boiling point 77° C.) used as an organic solvent was changed to 400 g (200 parts by weight per 100 parts by weight of the monomer mixture). From the resin particles thus manufactured, a powder makeup foundation, emulsion makeup foundation, and body powder were manufactured in the same manner as in example 1.

The resin particles obtained in example 3 were porous and had a volume-average particle diameter of 8.5 µm, a specific surface area of 223.7 $m^2/g$, and a bulk specific gravity of 0.333 g/mL.

The powder makeup foundation obtained in example 3 had a good makeup lasting time, a high spreadability on the skin, and a soft feel, and imparted a high soft-focus property and natural finish to the skin, making the skin look natural.

The emulsion makeup foundation obtained in example 3 had a good makeup lasting time and a smooth feel, and imparted a high soft-focus property and natural finish to the skin, making the skin look natural.

The body powder obtained in example 3 had a high spreadability on the skin and imparted a dry feeling to the skin.

Example 4

Resin particles were manufactured in the same manner as in example 1, except that the amount of methyl methacrylate used as a monofunctional (meth)acrylic acid ester was changed to 80 g (40 wt % of the whole monomer mixture), the amount of ethylene glycol dimethacrylate (EGDMA) used as a crosslinking monomer was changed to 120 g (60 wt % of the whole monomer mixture), and the ethyl acetate (boiling point 77° C.) (400 g, or 200 parts by weight per 100 parts by weight of the monomer mixture) as an organic solvent was replaced with toluene (boiling point 110° C.) (400 g, or 200 parts by weight per 100 parts by weight of the monomer mixture). From the resin particles thus manufactured, a powder makeup foundation, emulsion makeup foundation, and body powder were manufactured in the same manner as in example 1.

The resin particles obtained in example 4 were porous and had a volume-average particle diameter of 7.7 µm, a specific surface area of 237.1 $m^2/g$, and a bulk specific gravity of 0.359 g/mL.

The powder makeup foundation obtained in example 4 had a good makeup lasting time, a high spreadability on the skin, and a soft feel, and imparted a high soft-focus property and natural finish to the skin, making the skin look natural.

The emulsion makeup foundation obtained in example 4 had a good makeup lasting time and a smooth feel, and imparted a high soft-focus property and natural finish to the skin, making the skin look natural.

The body powder obtained in example 4 had a high spreadability on the skin and imparted a dry feeling to the skin.

Example 5

Resin particles were manufactured in the same manner as in example 1, except that the amount of methyl methacrylate used as a monofunctional (meth)acrylic acid ester was changed to 60 g (40 wt % of the whole monomer mixture), the ethylene glycol dimethacrylate (EGDMA) (100 g) as a crosslinking monomer was replaced with trimethylolpropane trimethacrylate (TMP) (90 g, or 60 wt % of the whole monomer mixture), and the amount of ethyl acetate (boiling point 77° C.) used as an organic solvent was changed to 450 g (300 parts by weight per 100 parts by weight of the monomer mixture). From the resin particles thus manufactured, a powder makeup foundation, emulsion makeup foundation, and body powder were manufactured in the same manner as in example 1.

The resin particles obtained in example 5 were porous and had a volume-average particle diameter of 5.9 µm, a specific surface area of 295.1 $m^2/g$, and a bulk specific gravity of 0.293 g/mL.

The powder makeup foundation obtained in example 5 had a good makeup lasting time, a high spreadability on the skin, and a soft feel, and imparted a high soft-focus property and natural finish to the skin, making the skin look natural.

The emulsion makeup foundation obtained in example 5 had a good makeup lasting time and a smooth feel, and imparted a high soft-focus property and natural finish to the skin, making the skin look natural.

The body powder obtained in example 5 had a high spreadability on the skin and imparted a dry feeling to the skin.

Example 6

Resin particles were manufactured in the same manner as in example 1, except that the methyl methacrylate (100 g) as a monofunctional (meth)acrylic acid ester was replaced with ethyl methacrylate (60 g, or 40 wt % of the whole monomer mixture), the amount of ethylene glycol dimethacrylate (EGDMA) used as a crosslinking monomer was changed to 90 g (60 wt % of the whole monomer mixture), and the ethyl acetate (boiling point 77° C.) (400 g, or 200 parts by weight per 100 parts by weight of the monomer mixture) as an organic solvent was replaced with toluene (boiling point 110° C.) (450 g, or 300 parts by weight per 100 parts by weight of the monomer mixture). From the resin particles thus manufactured, a powder makeup foundation, emulsion makeup foundation, and body powder were manufactured in the same manner as in example 1.

The resin particles obtained in example 6 were porous and had a volume-average particle diameter of 6.7 μm, a specific surface area of 206.2 m$^2$/g, and a bulk specific gravity of 0.314 g/mL.

The powder makeup foundation obtained in example 6 had a good makeup lasting time, a high spreadability on the skin, and a soft feel, and imparted a high soft-focus property and natural finish to the skin, making the skin look natural.

The emulsion makeup foundation obtained in example 6 had a good makeup lasting time and a smooth feel, and imparted a high soft-focus property and natural finish to the skin, making the skin look natural.

The body powder obtained in example 6 had a high spreadability on the skin and imparted a dry feeling to the skin.

Comparative Example 1

Resin particles were manufactured in the same manner as in example 1, except that the amount of methyl methacrylate used as a monofunctional (meth)acrylic acid ester was changed to 180 g (60 wt % of the whole monomer mixture), the amount of ethylene glycol dimethacrylate (EGDMA) used as a crosslinking monomer was changed to 120 g (40 wt % of the whole monomer mixture), and the amount of ethyl acetate (boiling point 77° C.) used as an organic solvent was changed to 300 g (100 parts by weight per 100 parts by weight of the monomer mixture). From the resin particles thus manufactured, a powder makeup foundation, emulsion makeup foundation, and body powder were manufactured in the same manner as in example 1.

The resin particles obtained in comparative example 1 were porous and had a volume-average particle diameter of 7.9 μm, a specific surface area of 86.3 m$^2$/g, and a bulk specific gravity of 0.465 g/mL.

The powder makeup foundation obtained in comparative example 1 had a good soft-focus property, but a short makeup lasting time, a low spreadability on the skin, a low level of softness, and a poor feel.

The emulsion makeup foundation obtained in comparative example 1 had a good soft-focus property, but a short makeup lasting time, a low level of smoothness, and a poor feel.

The body powder obtained in example 1 had a low spreadability on the skin and hardly imparted a dry feeling to the skin.

Comparative Example 2

Resin particles were manufactured in the same manner as in example 1, except that the amount of methyl methacrylate used as a monofunctional (meth)acrylic acid ester was changed to 570 g (95 wt % of the whole monomer mixture), the amount of ethylene glycol dimethacrylate (EGDMA) used as a crosslinking monomer was changed to 30 g (5 wt % of the whole monomer mixture), and no ethyl acetate (boiling point 77° C.) as an organic solvent was used. From the resin particles thus manufactured, a powder makeup foundation, emulsion makeup foundation, and body powder were manufactured in the same manner as in example 1.

The resin particles obtained in comparative example 2 had a volume-average particle diameter of 8.5 μm, a specific surface area of 1.1 m$^2$/g, and a bulk specific gravity of 0.637 g/mL.

The powder makeup foundation obtained in comparative example 2 had a short makeup lasting time, a low spreadability on the skin, and a poor soft-focus property, failed to impart a natural finish to the skin or make the skin look natural, and had a low level of softness and no good feel.

The emulsion makeup foundation obtained in comparative example 2 had a poor soft-focus property and a short makeup lasting time, and failed to impart a natural finish to the skin or make the skin look natural, and had no smoothness and no good feel.

The body powder obtained in comparative example 2 had a low spreadability on the skin and hardly imparted a dry feeling to the skin.

Table 1 shows the amounts of the monomers (methyl methacrylate and ethylene glycol dimethacrylate (EGDMA)) and organic solvents used in the manufacture of resin particles, the results of measurement of the specific surface area of resin particles, the results of measurement of the pore volume of resin particles, the results of measurement of the average pore diameter of resin particles, the results of measurement of the oil absorption amount for resin particles, the results of measurement of the compression strength of resin particles, the results of evaluation of the light diffusion properties of resin particles, the results of measurement of the amount of residual alkyl methacrylate, and the results of the sensory tests for examples 1 to 6 and comparative example 1 and 2. In Table 1, the light diffusion properties are represented by the intensities of reflections, at the 0°, +25°, +45°, and +75° reflection angles, of light that is incident at an angle of −45°. The intensity of each reflection in a reflection angle (0°, +25°, +45°, and +75°) in Table 1 is given relative to the intensity of 100 of the reflected light at the reflection angle of +45°.

TABLE 1

| | Component | Composition | Ex. 1 | Ex. 2 | Ex. 3 | Ex. 4 | Ex. 5 | Ex. 6 | Comp. Ex. 1 | Comp. Ex. 2 |
|---|---|---|---|---|---|---|---|---|---|---|
| Amount Used (parts by weight) | Monomer Mixture | Methyl Methacrylate | 100 | 60 | 80 | 80 | 60 | 0 | 180 | 570 |
| | | Ethyl Methacrylate | 0 | 0 | 0 | 0 | 0 | 60 | 0 | 0 |
| | | EGDMA | 100 | 90 | 120 | 120 | 0 | 90 | 120 | 30 |
| | | TMP | 0 | 0 | 0 | 0 | 90 | 0 | 0 | 0 |
| | Organic Solvent | Ethyl Acetate | 400 | 450 | 400 | 0 | 450 | 0 | 300 | 0 |
| | | Toluene | 0 | 0 | 0 | 400 | 0 | 450 | 0 | 0 |
| Volume-average Particle Diameter (μm) | | | 8.2 | 8.0 | 8.5 | 7.7 | 5.9 | 6.7 | 7.9 | 8.5 |
| Specific Surface Area (m$^2$/g) | | | 195.5 | 244.7 | 223.7 | 237.1 | 295.1 | 206.2 | 86.3 | 1.1 |
| Pore Volume (mL/g) | | | 0.610 | 0.790 | 0.811 | 0.809 | 0.549 | 0.626 | 0.385 | 0.003 |

TABLE 1-continued

| Component | Composition | Ex. 1 | Ex. 2 | Ex. 3 | Ex. 4 | Ex. 5 | Ex. 6 | Comp. Ex. 1 | Comp. Ex. 2 |
|---|---|---|---|---|---|---|---|---|---|
| Average Pore Diameter (nm) | | 13.8 | 14.0 | 15.7 | 14.2 | 13.5 | 11.4 | 16.6 | 13.0 |
| Oil Absorption Amount (mL/100 g) | | 224 | 544 | 346 | 310 | 282 | 540 | 156 | 77 |
| Compression Strength (MPa) | | 5.98 | 4.02 | 3.80 | 4.00 | 4.13 | 3.79 | 8.60 | 27.90 |
| Bulk Specific Gravity (g/mL) | | 0.385 | 0.306 | 0.333 | 0.359 | 0.293 | 0.314 | 0.465 | 0.637 |
| Amount of Residual Alkyl Methacrylate (ppm) | | * | * | * | * | * | * | * | 3514 |
| Light Diffusion | 0° | 57.3 | 72.3 | 69.1 | 47.5 | 62.1 | 60.4 | 47.2 | 37.2 |
| Properties | +25° | 70.7 | 82.2 | 79.2 | 62.3 | 75.2 | 73.8 | 62.2 | 60.5 |
| | +45° | 100.0 | 100.0 | 100.0 | 100.0 | 100.0 | 100.0 | 100.0 | 100.0 |
| | +75° | 46.5 | 54.0 | 49.5 | 38.1 | 48.1 | 47.7 | 40.0 | 53.9 |
| Power Makeup | Soft-focus Property | A | A | A | B | A | A | B | D |
| Foundation | Makeup Lasting Time | B | A | B | B | A | A | C | D |
| | Spreadability | B | A | A | B | B | B | C | D |
| | Softness | B | A | A | A | B | B | C | D |
| Emulsion Makeup | Soft-focus property | B | A | B | B | A | A | B | D |
| Foundation | Makeup lasting time | B | A | A | A | A | A | C | D |
| | Smoothness | B | B | B | B | B | B | C | D |
| Body Powder | Spreadability | B | A | A | B | B | B | C | D |
| | Dry feeling | A | A | A | B | A | A | C | D |

* Less than quantifiable minimum amount (30 ppm)

Table 1 shows that the resin particles of examples 1 to 6 of the present invention have a specific surface area of 190 m$^2$/g to 300 m$^2$/g (specifically, 195.5 m$^2$/g to 295.1 m$^2$/g), hence good light diffusion and oil absorbing properties.

Specifically, the resin particles of examples 1 to 6 have a higher oil absorption amount (224 mL/100 g to 544 mL/100 g) than the oil absorption amounts (77 mL/100 g to 156 mL/100 g) of the resin particles of comparative examples 1 and 2 which have a specific surface area of less than 190 m$^2$/g. Therefore, the resin particles of examples 1 to 6 absorb more sebum and improve the makeup lasting times of the powder makeup foundation and emulsion makeup foundation better than the resin particles of comparative examples 1 and 2. The resin particles of examples 1 to 6, when compounded into body powder, absorb more sebum and impart a silkier feel to the skin than the resin particles of comparative examples 1 and 2.

The resin particles of examples 1 to 6 reflect, in the 0° direction with an intensity of 45 or greater (specifically, 47.5° to 72.30), light that is incident thereto at an angle of −45°. The resin particles of examples 1 to 6 therefore impart a soft-focus property to cosmetic preparations, such as powder makeup foundations and emulsion makeup foundations. Especially, the resin particles of examples 1 to 3, 5, and 6 reflect light in all the 0°, +25°, and +75° reflection angles with an intensity of 45 or greater and therefore impart a very good soft-focus property to powder makeup foundations.

The resin particles of examples 1 to 6 have a lower bulk specific gravity (0.293 g/mL to 0.385 g/mL) than the bulk specific gravities (0.465 g/mL to 0.637 g/mL) of the resin particles of comparative examples 1 and 2. Therefore, the resin particles of examples 1 to 6 improve the spreadability of powder makeup foundations and body powder better than the resin particles of comparative examples 1 and 2.

The resin particles of examples 1 to 6 have a lower compression strength (3.79 MPa to 5.98 MPa) than the compression strengths (8.60 MPa to 27.90 MPa) of the resin particles of comparative examples 1 and 2. Therefore, the resin particles of examples 1 to 6 impart a higher level of softness to powder makeup foundations and a higher level of smoothness to emulsion makeup foundations than the resin particles of comparative examples 1 and 2.

The amounts of unreacted, residual alkyl methacrylate, such as methyl methacrylate and ethyl methacrylate, (amounts of residual alkyl methacrylate) in the resin particles of examples 1 to 6 were less than the quantifiable minimum amount (30 ppm). The resin particles of examples 1 to 6 contain a smaller amount of unreacted alkyl methacrylate (monofunctional (meth)acrylic acid ester) as shown here. The resin compositions obtained by kneading the resin particles into a base resin, when molded into a molded object by, for example, extrusion molding or injection molding, have a fewer molding defects, such as yellowing and gum.

Example 7

Exemplary Manufacturing of Optical Film

The resin particles (porous resin particles) obtained in example 2 (5 parts by weight), 29 parts by weight of an acrylic resin (trade name: Medium VM(K), manufactured by Dainichiseika Color & Chemicals Mfg. Co., Ltd., solid content 32%) as a binder resin, and 41 parts by weight of toluene were mixed. The mixture was stirred in a centrifugal stirrer for 3 minutes to obtain a coating agent. Thereafter, the obtained coating agent was applied onto a PET film as a base material using a 50-μm coater. The obtained film was dried for 1 hour in a drier maintained at 70° C., to obtain an optical film. The haze, total light transmittance, and gloss (matting properties) of the obtained optical film were measured. Results are shown in Table 2.

Example 8

Exemplary Manufacturing of Optical Film

An optical film was obtained in the same manner as in example 7, except that a coating agent was used that was obtained by mixing 1 part by weight of the resin particles (porous resin particles) obtained in example 2, 29 parts by weight of an acrylic resin (trade name: Medium VM(K), manufactured by Dainichiseika Color & Chemicals Mfg. Co., Ltd., solid content 32%) as a binder resin, and 41 parts by weight of toluene and stirring the mixture in a centrifugal stirrer for 3 minutes. The haze, total light transmittance, and gloss of the obtained optical film were measured. Results are shown in Table 3.

Comparative Example 3

Exemplary Manufacturing of Comparative Optical Film

An optical film was obtained in the same manner as in example 7, except that the resin particles obtained in example 2 were replaced with the resin particles obtained in comparative example 1. The haze, total light transmittance, and gloss (matting properties) of the obtained optical film were measured. Results are shown in Table 2.

Comparative Example 4

Exemplary Manufacturing of Comparative Optical Film

An optical film was obtained in the same manner as in example 7, except that the resin particles obtained in example 2 were replaced with the resin particles obtained in comparative example 2. The haze, total light transmittance, and gloss (matting properties) of the obtained optical film were measured. Results are shown in Table 2.

Comparative Example 5

Exemplary Manufacturing of Comparative Optical Film

An optical film was obtained in the same manner as in example 8, except that the resin particles obtained in example 2 were replaced with the resin particles obtained in comparative example 1. The haze, total light transmittance, and gloss (matting properties) of the obtained optical film were measured. Results are shown in Table 3.

Comparative Example 6

Exemplary Manufacturing of Comparative Optical Film

An optical film was obtained in the same manner as in example 8, except that the resin particles obtained in example 2 were replaced with the resin particles obtained in comparative example 2. The haze, total light transmittance, and gloss (matting properties) of the obtained optical film were measured. Results are shown in Table 3.

Method of Measuring Total Light Transmittance and Haze

The haze and total light transmittance of the optical films obtained in examples 7 to 8 and comparative examples 3 to 6 were measured using a haze meter "NDH-4000" manufactured by Nippon Denshoku Industries Co., Ltd. The measurement of total light transmittance was carried out in accordance with JIS K 7361-1. The measurement of haze was carried out in accordance with JIS K 7136. The haze and total light transmittance shown in Tables 2 and 3 are averages of measurements of two measurement samples (number of measurement samples n=2). The haze level increases with an increase in the diffusibility of the light having transmitted through the optical film (transmitted light).

Method of Measuring Gloss

The glosses of the optical films obtained in examples 7 to 8 and comparative examples 3 to 6 were measured using a gloss checker (gloss meter) "IG-331" manufactured by Horiba, Ltd. Specifically, the gloss of the optical film at 60° was measured using a gloss checker (gloss meter) "IG-331" in accordance with the method prescribed in JIS Z8741. The gloss level decreases with an increase in the diffusibility of the light having reflected off the surface of the optical film (specifically, the surface, of the coating film, that is coated with a coating agent). A lower gloss level indicates better matting properties.

TABLE 2

|  | Ex. 7 | Comp. Ex. 3 | Comp. Ex. 4 |
|---|---|---|---|
| Haze (%) | 76.0 | 72.2 | 61.0 |
| Total Light Transmittance (%) | 76.8 | 80.6 | 84.5 |
| Gloss (60°) | 11.3 | 16.3 | 24.7 |

TABLE 3

|  | Ex. 8 | Comp. Ex. 5 | Comp. Ex. 6 |
|---|---|---|---|
| Haze (%) | 43.1 | 40.2 | 24.1 |
| Total Light Transmittance (%) | 85.7 | 86.6 | 88.9 |
| Gloss (60°) | 37.3 | 54.3 | 98.0 |

The rate of resin particle content of the coating agent used in the manufacture of the optical film of example 7 is equal to the rate of resin particle content of the coating agent used in the manufacture of the optical films of comparative examples 3 and 4. As shown in Table 2, the optical film of example 7 manufactured from the resin particles obtained in example 2 as resin particles has a higher level of haze and a lower level of gloss than the optical films of comparative examples 3 and 4 manufactured from the resin particles of comparative examples 1 and 2 as resin particles.

The rate of resin particle content of the coating agent used in the manufacture of the optical film of example 8 is equal to the rate of resin particle content of the coating agent used in the manufacture of the optical films of comparative examples 5 and 6. As shown in Table 3, the optical film of example 8 manufactured from the resin particles obtained in example 2 as resin particles has a higher level of haze and a lower level of gloss than the optical films of comparative examples 5 and 6 manufactured from the resin particles of comparative examples 1 and 2 as resin particles. These results show that the optical film of example 8 have better light diffusion and matting properties than the optical films of comparative examples 5 and 6.

That clearly indicates that the resin particles obtained in example 2 impart better light diffusion and matting properties to the optical film than do the resin particles obtained in comparative examples 1 and 2.

The present invention may be implemented in various forms without departing from its spirit and main features. Therefore, the aforementioned examples are for illustrative purposes only in every respect and should not be subjected to any restrictive interpretations. The scope of the present invention is defined only by the claims and never bound by the specification. Those modifications and variations that may lead to equivalents of claimed elements are all included within the scope of the invention.

The present application hereby claims priority on Japanese Patent Application, Tokugan, No. 2012-212419 filed Sep. 26, 2012 in Japan, the entire contents of which are hereby incorporated herein by reference.

REFERENCE SIGNS LIST

1 Test Piece
2 Resin Particles

3 Double-sided Adhesive Tape
4 Hiding Paper
5 Incident Light Ray (−45°)
6 Reflected Light Ray

The invention claimed is:

1. Porous resin particles which comprise a polymer of a monomer mixture,
the monomer mixture being
(1) a mixture consisting of a methacrylic acid ester and a crosslinking monomer, the methacrylic acid ester being selected from the group consisting of methyl methacrylate and ethyl methacrylate, or
(2) a mixture consisting of a methacrylic acid ester, a crosslinking monomer, and another monomer, the methacrylic acid ester being selected from the group consisting of methyl methacrylate and ethyl methacrylate, the another monomer is neither a monofunctional (meth)acrylic acid ester nor the crosslinking monomer,
the methacrylic acid ester accounting for 1 wt % to 50 wt % of the monomer mixture,
the crosslinking monomer accounting for 50 wt % to 99 wt % of the monomer mixture, and
the porous resin particles having a specific surface area of 190 $m^2/g$ to 300 $m^2/g$ and a bulk specific gravity of 0.25 g/mL to 0.45 g/mL.

2. The porous resin particles as set forth in claim 1, wherein the crosslinking monomer is a (meth)acrylic-based crosslinking monomer.

3. The porous resin particles as set forth in claim 1, having an oil absorption amount of 200 mL/100 g to 700 mL/100 g.

4. The porous resin particles as set forth in claim 1, having a pore volume of 0.4 mL/g to 0.9 mL/g.

5. The porous resin particles as set forth in claim 1, having a compression strength of 3.0 MPa to 7.0 MPa when compressed by 10%.

6. An external preparation which comprises the porous resin particles set forth in claim 1.

7. A coating agent which comprises the porous resin particles set forth in claim 1.

8. An optical film which comprises a base material and the coating agent set forth in claim 7, the base material being coated with the coating agent.

9. A resin composition which comprises a base resin and the porous resin particles set forth in claim 1.

10. A molded object which comprises the resin composition set forth in claim 9, the resin composition being molded into the molded object.

11. Porous resin particles which comprise a polymer of a monomer mixture,
the monomer mixture being
(1) a mixture consisting of a methacrylic acid ester and a crosslinking monomer, the methacrylic acid ester being selected from the group consisting of methyl methacrylate and ethyl methacrylate, or
(2) a mixture consisting of a methacrylic acid ester, a crosslinking monomer, and another monomer, the methacrylic acid ester being selected from the group consisting of methyl methacrylate and ethyl methacrylate, the another monomer is neither a monofunctional (meth)acrylic acid ester nor the crosslinking monomer,
the porous resin particles having a specific surface area of 190 $m^2/g$ to 300 $m^2/g$ and such optical properties that the porous resin particles reflect, in a 0° direction with an intensity of 45 or greater, light that is incident thereto at an angle of −45°, where the porous resin particles specularly reflect, in a +45° direction with an intensity of 100, light that is incident thereto at an angle of −45°.

12. The porous resin particles as set forth in claim 11, having an oil absorption amount of 200 mL/100 g to 700 mL/100 g.

13. The porous resin particles as set forth in claim 11, having a pore volume of 0.4 mL/g to 0.9 mL/g.

14. The porous resin particles as set forth in claim 11, having a compression strength of 3.0 MPa to 7.0 MPa when compressed by 10%.

15. An external preparation which comprises the porous resin particles set forth in claim 11.

16. A coating agent which comprises the porous resin particles set forth in claim 11.

17. An optical film which comprises a base material and the coating agent set forth in claim 16, the base material being coated with the coating agent.

18. A resin composition which comprises a base resin and the porous resin particles set forth in claim 11.

19. A molded object which comprises the resin composition set forth in claim 18, the resin composition being molded into the molded object.

20. A method of manufacturing porous resin particles which comprises:
the polymerization step of suspension polymerizing a monomer mixture in an aqueous medium in the presence of an organic solvent to prepare a suspension containing porous resin particles, the monomer mixture being (1) a mixture consisting of 1 wt % to 50 wt % of a methacrylic acid ester and 50 wt % to 99 wt % of a crosslinking monomer, the methacrylic acid ester being selected from the group consisting of methyl methacrylate and ethyl methacrylate, or (2) a mixture consisting of 1 wt % to 50 wt % of a methacrylic acid ester, 50 wt % to 99 wt % of a crosslinking monomer, and another monomer, the methacrylic acid ester being selected from the group consisting of methyl methacrylate and ethyl methacrylate, the another monomer is neither a monofunctional (meth)acrylic acid ester nor the crosslinking monomer; and
the distillation step of distilling the suspension to remove the organic solvent from the suspension after the polymerization step,
the organic solvent being used in 180, exclusive, to 450 parts by weight per 100 parts by weight of the monomer mixture in the polymerization step.

21. The method of manufacturing porous resin particles as set forth in claim 20, wherein the organic solvent has a boiling point of 69 to 90° C.

22. The method of manufacturing porous resin particles as set forth in claim 20, wherein the crosslinking monomer is a (meth)acrylic-based crosslinking monomer.

* * * * *